US008168821B2

(12) United States Patent
Becker et al.

(10) Patent No.: US 8,168,821 B2
(45) Date of Patent: May 1, 2012

(54) CYCLOPROPYLACETIC ACID DERIVATIVES AND USE THEREOF

(75) Inventors: Eva-Maria Becker, Wuppertal (DE); Michael Hahn, Langenfeld (DE); Andreas Knorr, Erkrath (DE); Christian Pilger, Ludwigshafen (DE); Johannes-Peter Stasch, Solingen (DE); Karl-Heinz Schlemmer, Wuppertal (DE); Frank Wunder, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 498 days.

(21) Appl. No.: 12/083,761

(22) PCT Filed: Oct. 9, 2006

(86) PCT No.: PCT/EP2006/009723

§ 371 (c)(1),
(2), (4) Date: May 19, 2009

(87) PCT Pub. No.: WO2007/045367

PCT Pub. Date: Apr. 26, 2007

(65) Prior Publication Data

US 2009/0286882 A1    Nov. 19, 2009

(30) Foreign Application Priority Data

Oct. 21, 2005  (DE) .......................... 10 2005 050 498

(51) Int. Cl.
*C07C 65/00* (2006.01)
*C07C 59/48* (2006.01)

(52) U.S. Cl. ........................ 562/473; 562/471
(58) Field of Classification Search .................. 562/471, 562/473

See application file for complete search history.

(56) References Cited

U.S. PATENT DOCUMENTS

| 6,180,656 B1 | 1/2001 | Furstner et al. |
| 6,387,940 B1 | 5/2002 | Straub et al. |
| 6,410,740 B1 | 6/2002 | Straub et al. |
| 6,414,009 B1 | 7/2002 | Straub et al. |
| 6,451,805 B1 | 9/2002 | Straub et al. |
| 6,462,068 B1 | 10/2002 | Straub et al. |
| 6,864,287 B1 | 3/2005 | Alonso-Alija et al. |
| 7,087,644 B1 | 8/2006 | Alonso-Alija et al. |
| 7,674,825 B2 | 3/2010 | Alonso-Alija et al. |
| 7,998,988 B2 | 8/2011 | Bartel et al. |
| 2004/0082798 A1 | 4/2004 | Alonso-Alija et al. |
| 2004/0176446 A1 | 9/2004 | Alonso-Alija et al. |
| 2007/0179139 A1 | 8/2007 | Alonso-Alija et al. |
| 2008/0058314 A1 | 3/2008 | Alonso-Alija et al. |

FOREIGN PATENT DOCUMENTS

| EP | 0341551 A1 | 11/1989 |
| WO | WO-98/16223 A1 | 4/1998 |
| WO | WO-98/16507 A2 | 4/1998 |
| WO | WO-98/23619 A1 | 6/1998 |
| WO | WO-01/19355 A2 | 3/2001 |
| WO | WO-01/19776 | 3/2001 |
| WO | WO-01/19778 | 3/2001 |
| WO | WO-01/19780 A2 | 3/2001 |
| WO | WO-02/070462 A1 | 9/2002 |
| WO | WO-02/070510 A2 | 9/2002 |

OTHER PUBLICATIONS

FN Ko et al.: "YC-1, A Novel Activator of Platelet Guanylate Cyclase," Blood, 84, 1994, pp. 4226-4233.
A. Mulsch et al.: "Effect of YC-1, an NO-independent, superoxide-Sensitive Stimulator of Soluble Guanylyl Cyclase, on Smooth Muscle Responsiveness to Nitrovasodilators," British Journal of Pharmacology, 120, 1997, pp. 681-689.
D. B. Glass et al.: "Stimulation of Human Platelet Guanylate Cyclase by Fatty Acids," The Journal of Biological Chemistry, vol. 252, No. 4, Feb. 25, 1977, pp. 1279-1285.
D. J. Pettibone et al.: "A Structurally Novel Stimulator of Guanylate Cyclase with Long-Lasting Hypotensive Activity in the Dog," European Journal of Pharmacology, 116, 1985, pp. 307-312.
S-M Yu et al.: "Vasorelaxant Effect of Isoliquiritigenin, a Novel Soluble Guanylate Cyclase Activator, in Rat Aorta," British Journal of Pharmacology, 114, 1995, pp. 1587-1594.
R. Gerzer et al.: "Soluble Guanylate Cyclase Purified from Bovine Lung Contains Heme and Copper," FEBS Letters, vol. 132, No. 1, Sep. 1981, pp. 71-74.
M. Hoenicka et al.: "Purified Soluble Guanylyl Cyclase Expressed in a Baculovirus/Sf9 System: Stimulation by YC-1, Nitirc Oxide, and Carbon Monoxide," J. Mol. Med, 77, 1999, pp. 14-23.
L. J. Ignarro: "Regulation of Cytosolic Guanylyl Cyclase by Porphyrins and Metalloporphyrins," Advances in Pharmacology, vol. 26, 1994, pp. 35-65.
U.S. Appl. No. 12/083,814, filed in Oct. 19, 2009.
U.S. Appl. No. 12/085,543, filed Feb. 17, 2009.
U.S. Appl. No. 12/083,509, filed Jul. 6, 2009.
U.S. Appl. No. 12/529,342, filed Mar. 25, 2010.
Demko, et al., "Preparation of 5-substituted 1H-tetrazoles from nitriles in water," J. Org. Chem. 2001, 66: 7945-7950.
Patani et al., "Bioisterism: A rational Approach in Drug Design," Chem. Rev., 1996, 96: 3147-3176.

*Primary Examiner* — Jafar Parsa
(74) *Attorney, Agent, or Firm* — Karen B. King

(57) ABSTRACT

The present application relates to novel cyclopropylacetic acid derivatives, to processes for their preparation, to their use for the treatment and/or prophylaxis of diseases and to their use for preparing medicaments for the treatment and/or prophylaxis of diseases, in particular for the treatment and/or prevention of cardiovascular disorders.

6 Claims, No Drawings

CYCLOPROPYLACETIC ACID DERIVATIVES AND USE THEREOF

RELATED APPLICATIONS/PATENTS AND INCORPORATION BY REFERENCE

This application is a National Stage Application filed under 35 U.S.C. §371 based on International Application No. PCT/EP2006/009723, filed Oct. 9, 2006, which claims priority to German Patent Application Numbers 102005050498.1, filed Oct. 21, 2005, the entire contents of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel cyclopropylacetic acid derivatives, to processes for their preparation, to their use for the treatment and/or prophylaxis of diseases and to their use for preparing medicaments for the treatment and/or prophylaxis of diseases, in particular for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole [YC-1, Wu et al., Blood 84 (1994), 4226, Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223, WO 98/16507 and WO 98/23619).

The above-described stimulators of soluble guanylate cyclase stimulate the enzyme either directly via the heme group (carbon monoxide, nitric oxide or diphenyliodonium hexafluorophosphate) by interacting with the iron center of the heme group and a change in conformation which results therefrom and leads to an increase in the enzymic activity [Gerzer et al., FEBS Lett. 132 (1981), 71] or via a heme-dependent mechanism which is independent of NO but leads to a potentiation of the stimulating effect of NO or CO [e.g. YC-1, Hoenicka et al., J. Mol. Med. 77 (1999) 14; or the pyrazole derivatives described in WO 98/16223, WO 98/16507 and WO 98/23619].

It has not been possible to confirm the stimulating effect, asserted in the literature, of isoliquiritigenin and of fatty acids such as, for example, of arachidonic acid, prostaglandin endoperoxides and fatty acid hydroperoxides on soluble guanylate cyclase [cf., for example, Hoenicka et al., J. Mol. Med. 77 (1999), 14].

If the heme group is removed from soluble guanylate cyclase, the enzyme still shows a detectable basal catalytic activity, i.e. cGMP is still produced. The remaining basal catalytic activity of the heme-free enzyme cannot be stimulated by any of the aforementioned known stimulators.

Stimulation of heme-free soluble guanylate cyclase by protoporphyrin IX has been described [Ignarro et al., Adv. Pharmacol. 26 (1994), 35]. However, protoporphyrin IX can be regarded as a mimic of the NO-heme adduct, which is why addition of protoporphyrin IX to soluble guanylate cyclase ought to lead to production of a structure of the enzyme corresponding to the heme-containing soluble guanylate cyclase which is stimulated by NO. This is also verified by the fact that the stimulating effect of protoporphyrin IX is increased by the NO-independent but heme-dependent stimulator YC-1 described above [Mülsch et al., Naunyn Schmiedebergs Arch. Pharmacol. 355, R47].

In contrast to the above-described stimulators of soluble guanylate cyclase, the compounds of the present invention are able to activate both the heme-containing and the heme-free form of soluble guanylate cyclase. Thus, with these novel activators, the enzyme is stimulated via a heme-independent pathway, which is also verified by the facts that the novel activators firstly show no synergistic effect with NO on the heme-containing enzyme, and secondly the effect of these novel activators cannot be blocked by the heme-dependent inhibitor of soluble guanylate cyclase 1H-1,2,4-oxadiazole-(4,3-a)-quinoxalin-1-one (ODQ).

EP 0 341 551-A1 discloses alkenoic acid derivatives as leucotriene antagonists for the treatment of disorders of the circulatory and respiratory systems. WO 01/19355, WO 01/19776, WO 01/19778, WO 01/19780, WO 02/070462 and WO 02/070510 describe dicarboxylic acid and amino dicarboxylic acid derivatives as stimulators of soluble guanylate cyclase for the treatment of cardiovascular disorders. However, it has emerged that these compounds have disadvantages in relation to their pharmacokinetic properties, such as, in particular, a low bioavailability and/or an only short duration of action after oral administration.

It was therefore an object of the present invention to provide novel compounds which act as activators of soluble guanylate cyclase but do not have the aforementioned disadvantages of the prior art compounds.

This object is achieved by the compounds described in the present invention. These compounds are distinguished structurally from the prior art compounds by a 1,4-diphenylbut-1-en-3-yl or 1,5-diphenylpent-1-en-3-yl core structure associated with a cyclopropylacetic acid side chain.

Specifically, the present invention relates to compounds of the general formula (I)

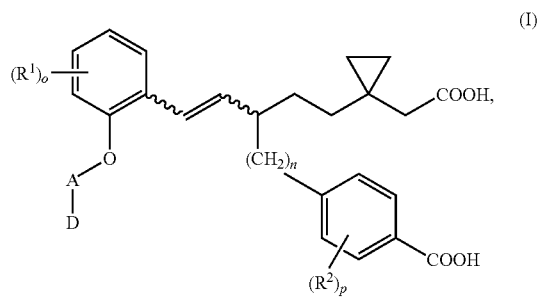

in which
A represents a bond, $(C_1\text{-}C_7)$-alkanediyl, $(C_2\text{-}C_7)$-alkenediyl or $(C_2\text{-}C_7)$-alkynediyl,
D represents hydrogen, trifluoromethyl or a group of the formula

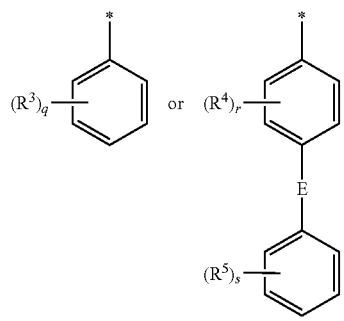

in which * represents the point of attachment to group A and
E represents a bond, $CH_2$, $-CH_2-CH_2-$ or $-CH=CH-$,
n represents the number 1 or 2,
$R^1$, $R^2$, $R^3$, $R^4$ and $R^5$ independently of one another represent a substituent selected from the group consisting of halogen, $(C_1\text{-}C_6)$-alkyl, trifluoromethyl, $(C_1\text{-}C_6)$-alkoxy, trifluoromethoxy, cyano and nitro,
and
o, p, q, r and s independently of one another each represent the number 0, 1, 2, 3 or 4,
where, if $R^1$, $R^2$, $R^3$, $R^4$ or $R^5$ occurs more than once, their meanings may in each case be identical or different,
and salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

The group

in formula (I) means that this CC double bond may be present in a cis or in a trans configuration. Both isomeric forms are encompassed by the present invention. Preferred compounds of the formula (I) have a trans arrangement of this double bond.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methyl-morpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

($C_1$-$C_6$)-Alkyl and ($C_1$-$C_4$) are in the context of the invention a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, iso-butyl, sec-butyl, tert-butyl, 1-ethylpropyl, n-pentyl and n-hexyl.

($C_1$-$C_7$)-Alkanediyl is in the context of the invention a straight-chain or branched divalent alkyl radical having 1 to 7 carbon atoms. A straight-chain alkanediyl radical having 1 to 6 carbon atoms is preferred. Examples which may be preferably mentioned are: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl.

($C_2$-$C_7$)-Alkenediyl is in the context of the invention a straight-chain or branched divalent alkenyl radical having 2 to 7 carbon atoms and up to 3 double bonds. A straight-chain alkenediyl radical having 2 to 6 carbon atoms and up to 2 double bonds is preferred. Examples which may be preferably mentioned are: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

($C_2$-$C_7$)-Alkynediyl is in the context of the invention a straight-chain or branched divalent alkynyl radical having 2 to 7 carbon atoms and up to 3 triple bonds. A straight-chain alkynediyl radical having 2 to 6 carbon atoms and up to 2 triple bonds is preferred. Examples which may be preferably mentioned are: ethyne-1,2-diyl, propyne-1,3-diyl, but-1-yne-1,4-diyl, but-1-yne-1,3-diyl, but-2-yne-1,4-diyl, pent-2-yne-1,5-diyl, pent-2-yne-1,4-diyl and hex-3-yne-1,6-diyl.

($C_1$-$C_6$)-Alkoxy and ($C_1$-$C_4$)-alkoxy are in the context of the invention a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, tert-butoxy, n-pentoxy and n-hexoxy.

($C_1$-$C_4$)-Alkoxycarbonyl is in the context of the invention a straight-chain or branched alkoxy radical having 1 to 4 carbon atoms which is linked via a carbonyl group. Examples which may be preferably mentioned are methoxycarbonyl, ethoxycarbonyl, n-propoxycarbonyl, isopropoxycarbonyl and tert-butoxycarbonyl.

Halogen in the context of the invention includes fluorine, chlorine, bromine and iodine. Chlorine or fluorine are preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one substituent is very particularly preferred.

Preference is given in the context of the present invention to compounds of the formula (I) in which
A represents a bond or ($C_1$-$C_7$)-alkanediyl,
D represents hydrogen, trifluoromethyl or a group of the formula

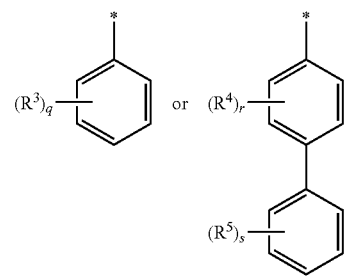

in which * represents the point of attachment to group A,
n represents the number 1 or 2,
$R^1$, $R^3$, $R^4$ and $R^5$ independently of one another represent a substituent selected from the group consisting of fluorine, chlorine, bromine, ($C_1$-$C_4$)-alkyl, trifluoromethyl, ($C_1$-$C_4$)-alkoxy and trifluoromethoxy,
o, q, r and s independently of one another each represent the number 0, 1 or 2,
where, if $R^1$, $R^3$, $R^4$ or $R^5$ occurs more than once, their meanings may in each case be identical or different,
$R^2$ represents fluorine
and
p represents the number 0 or 1,
and salts, solvates and solvates of the salts thereof.

Particular preference is given in the context of the present invention to compounds of the formula (I-A)

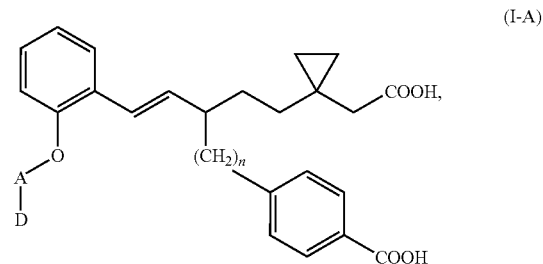

(I-A)

in which
A represents ($C_1$-$C_7$)-alkanediyl,
D represents hydrogen or a group of the formula

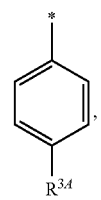

in which * represents the point of attachment to group A
and
$R^{3A}$ represents hydrogen, fluorine, chlorine, methyl, tert-butyl, trifluoromethyl, methoxy or trifluoromethoxy,
and
n represents the number 1 or 2,
and salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds according to the invention of the formula (I), characterized in that compounds of the formula (II)

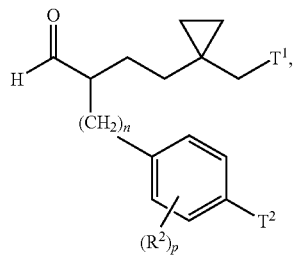
(II)

in which $R^2$, n and p each have the meanings given above and $T^1$ and $T^2$ are identical or different and represent cyano or $(C_1$-$C_4)$-alkoxycarbonyl, are either

[A] reacted in an inert solvent in the presence of a base with a compound of the formula (III-A)

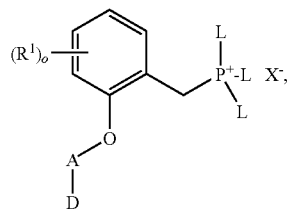
(III-A)

in which A, D, $R^1$ and o each have the meanings given above and

L represents phenyl or o-, m- or p-tolyl and

X represents halide or tosylate, to give compounds of the formula (IV-A)

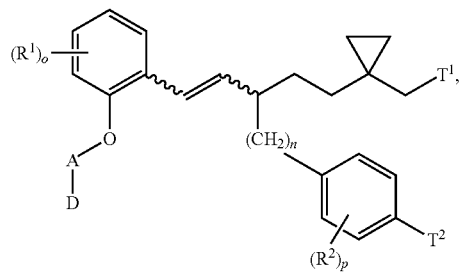
(IV-A)

in which A, D, $R^1$, $R^2$, n, o, p, $T^1$ and $T^2$ each have the meanings given above, or

[B] reacted in an inert solvent in the presence of a base with a compound of the formula (III-B)

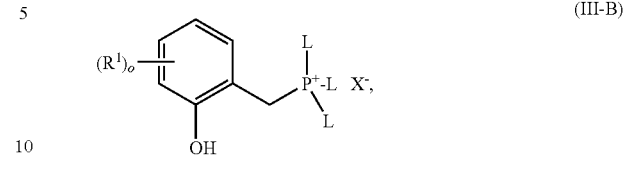
(III-B)

in which $R^1$, o, L and X each have the meanings given above, initially to give compounds of the formula (IV-B)

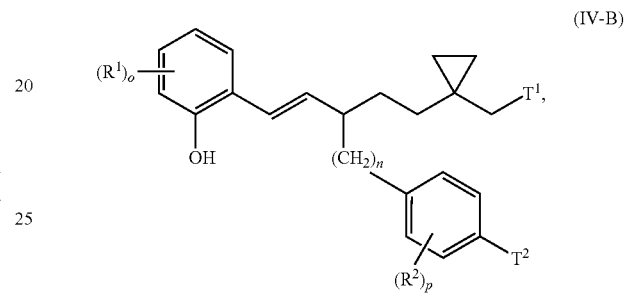
(IV-B)

in which $R^1$, $R^2$, n, o, p, $T^1$ and $T^2$ each have the meanings given above, and these compounds are then alkylated in an inert solvent in the presence of a base with a compound of the formula (V)

$$D-A^1-Q \qquad (V),$$

in which D has the meaning given above, $A^1$ has the meaning of A given above, but does not represent a bond, and Q represents a leaving group, such as, for example, halogen, tosylate or mesylate, to give compounds of the formula (IV-C)

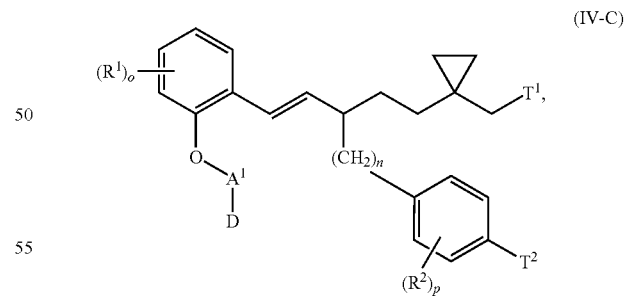
(IV-C)

in which $A^1$, D, $R^1$, $R^2$, n, o, p, $T^1$ and $T^2$ each have the meanings given above, and the resulting compounds of the formula (IV-A) or (V<C) are then converted by hydrolysis of the ester or nitrile groups $T^1$ and $T^2$ into the dicarboxylic acids of the formula (I)

and the compounds of the formula (I) are, if appropriate, separated into their enantiomers and/or diastereomers using methods known to the person skilled in the art and/or are, if appropriate, converted with the appropriate (i) solvents and/or (ii) bases or acids into their solvates, salts and/or solvates of the salts.

Inert solvents for process steps (II)+(III-A)→(IV-A) and (II)+(III-B)→(IV-B) are for example ethers, such as diethyl ether, tetrahydrofuran, glycol dimethyl ether or diethylene glycol dimethyl ether, or hydrocarbons such as benzene, toluene, xylene, pentane, hexane, heptane, cyclohexane or petroleum fractions, or mixtures of these solvents. Tetrahydrofuran mixed with hexane is preferably used.

Bases suitable for these process steps are the bases usual for a Wittig reaction. These include in particular strong bases such as n-, sec- or tert-butyllithium, lithiumdiisopropylamide (LDA) or lithium, sodium or potassium bis(trimethylsilyl)amide. n-Butyllithium is preferred.

The reactions (II)+(III-A)→(IV-A) and (II)+(III-B)→(IV-B) are generally carried out in a temperature range from −78° C. to +20° C., preferably at −20° C. to +10° C.

Inert solvents for the process step (IV-B)+(V)→(IV-C) are for example ethers such as diethyl ether, dioxane, tetrahydrofuran, glycol dimethyl ether or diethylene glycol dimethyl ether, or other solvents such as acetonitrile, dimethylformamide, dimethyl sulfoxide, N,N'-dimethylpropylene urea (DMPU) or N-methylpyrrolidone (NMP). It is likewise possible to employ mixtures of the solvents mentioned. Acetonitrile is preferably used.

Bases suitable for this process step are in particular potassium carbonate, sodium or potassium hydride, lithiumdiisopropylamide or n-butyllithium. Potassium carbonate is preferably used.

The reaction (IV-B)+(V)→(IV-C) is generally carried out in a temperature range from +20° C. to +120° C., preferably at +50° C. to +100° C.

Hydrolysis of the ester and nitrile groups $T^1$ and $T^2$ in process steps (IV-A)→(I) and (IV-C)→(I) takes place by usual methods, by treating the esters or nitrites in inert solvents with acids or bases, and in the latter case converting the initially produced salts into the free carboxylic acids by treatment with acid. In the case of the tert-butyl esters, the ester cleavage preferably takes place with acids.

If the groups $T^1$ and $T^2$ are different, the hydrolysis can where appropriate be carried out simultaneously in a one-pot reaction or in two separate reaction steps.

Inert solvents suitable for these reactions are water or the organic solvents usual for an ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulfoxide. It is likewise possible to employ mixtures of the solvents mentioned. In the case of a basic ester hydrolysis, mixtures of water with dioxane, tetrahydrofuran, methanol and/or ethanol are preferably employed, and in the case of nitrile hydrolysis preferably water or n-propanol. In the case of reaction with trifluoroacetic acid, preferably dichloromethane, and in the case of reaction with hydrogen chloride preferably tetrahydrofuran, diethyl ether, dioxane or water, is used.

Suitable bases are the usual inorganic bases. These preferably include alkali metal or alkaline earth metal hydroxides such as, for example, sodium, lithium, potassium or barium hydroxide, or alkali metal or alkaline earth metal carbonates such as sodium, potassium or calcium carbonate. Sodium, potassium or lithium hydroxide are particularly preferred.

Suitable acids for the ester cleavage are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof where appropriate with addition of water. Hydrogen chloride or trifluoroacetic acid in the case of the tert-butyl esters and hydrochloric acid in the case of the methyl esters are preferred.

The ester cleavage generally takes place in a temperature range from 0° C. to +100° C., preferably at +20° C. to +60° C. The nitrile hydrolysis is generally carried out in a temperature range from +50° C. to +150° C., preferably at +90° C. to +110° C.

The reactions mentioned can be carried out under atmospheric, elevated or reduced pressure (e.g. from 0.5 to 5 bar). They are generally carried out under atmospheric pressure in each case.

The aldehydes of the formula (II) can be prepared in analogy to processes disclosed in the literature, for example by a sequential dialkylation of diallyl malonate with compounds of the formulae (VI) and (VII)

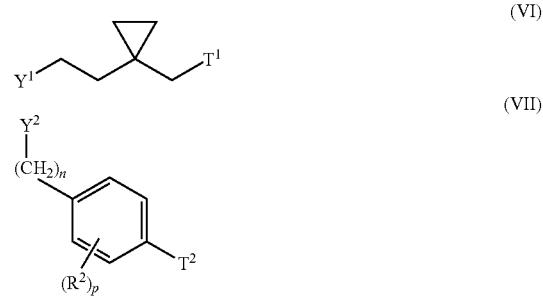

in which $R^2$, n, p, $T^1$ and $T^2$ each have the meanings indicated above, and
$Y^1$ and $Y^2$ are identical or different and are a leaving group such as, for example, halogen, mesylate or tosylate,
to give compounds of the formula (VIII)

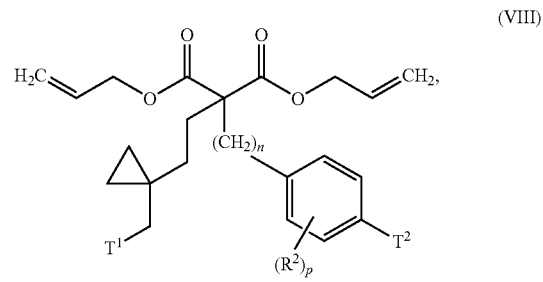

in which $R^2$, n, p, $T^1$ and $T^2$ each have the meanings indicated above,
subsequent ester cleavage to give compounds of the formula (IX)

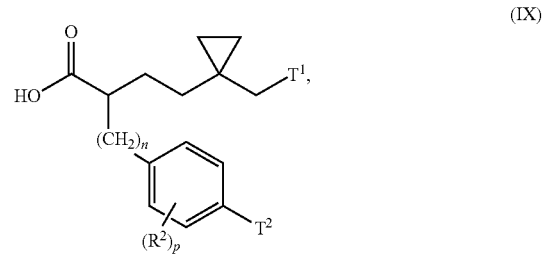

in which $R^2$, n, p, $T^1$ and $T^2$ each have the meanings indicated above, and subsequent reduction of the carboxylic acid grouping (see also reaction schemes 2 and 3 below).

The compounds of the formulae (III-A) and (III-B) can be obtained by processes usual in the literature by reaction of compounds of the formula (X-A) or (X-B)

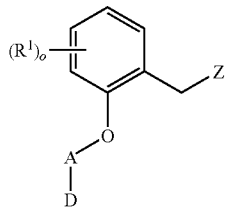
(X-A)

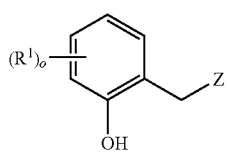
(X-B)

in which A, D, $R^1$ and o each have the meanings indicated above, and

Z is a leaving group such as, for example, halogen or tosylate, or is hydroxy, with, for example, triphenylphosphine or (in the case of Z=OH) triphenylphosphine hydrobromide (see also reaction scheme 4 below).

The compounds of the formula (VI) can be obtained analogously to processes known from the literature, for example from cyclopropanone acetals via a Wittig reaction, subsequent Michael addition, hydroboration and halogenation (see reaction scheme 1 below).

The compounds of the formulae (V), (VII), (X-A) and (X-B) are commercially available, disclosed in the literature or can be prepared in analogy to processes disclosed in the literature (concerning the preparation of the compounds according to the invention overall, compare also the preparation processes described in EP 0 341 551-A1, WO 01/19355, WO 01/19776 and WO 01/19778).

Separation of the compounds according to the invention into the corresponding enantiomers and/or diastereomers can take place where appropriate, depending on expediency, even at the stage of the compounds (IV-A), (IV-B), (IV-C) or (IX), which are then reacted further in separated form in accordance with the process sequence described above. Such a fractionation of the stereoisomers can be carried out by usual methods known to the skilled person; chromatographic processes or separation via diastereomeric salts are preferably used.

Preparation of the compounds according to the invention can be illustrated by the following synthesis schemes:

Scheme 1

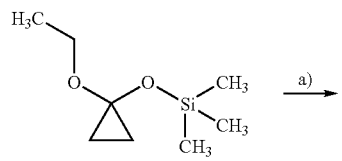

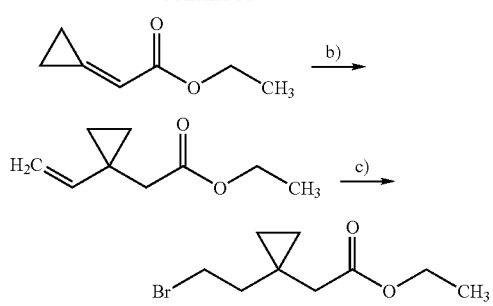

[a) $Ph_3P$=CHCOOEt, benzoic acid, toluene, 90° C., 18 h; b) vinylmagnesium chloride, copper(I) chloride, lithium chloride, THF, -78° C. → -5° C.; c) 1. borane-THF complex, THF, 0° C. → RT, 1h; 2. bromine, sodium methoxide, methanol, -5° C.].

Scheme 2

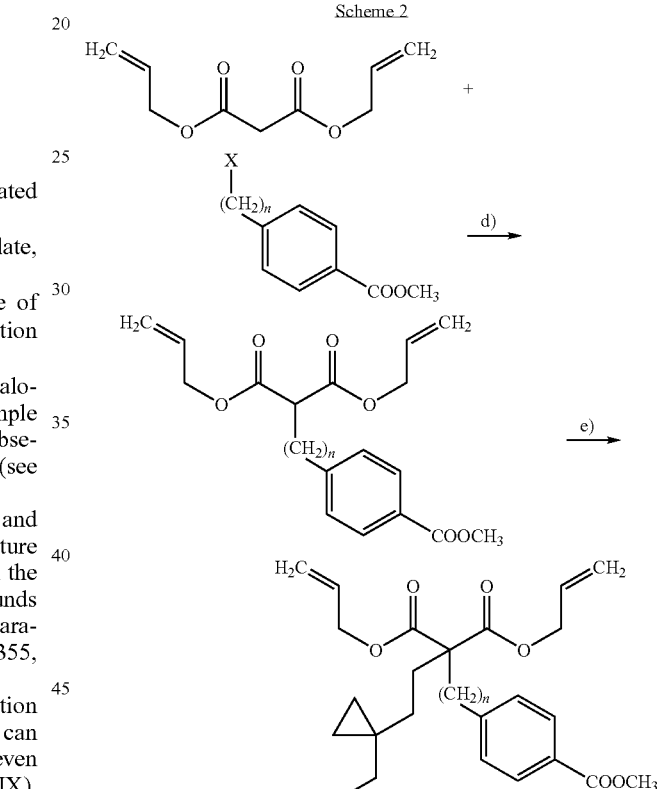

[X = Cl or Br, n = 1 or 2; d) sodium hydride, dioxane or dioxane/THF, 0° C. → 40° C. → 110° C., 4-16 h; e) sodium hydride, ethyl [1-(2-bromoethyl)cyclopropyl]acetate, DMF, 0° C. → 100° C., 8-12 h].

Scheme 3

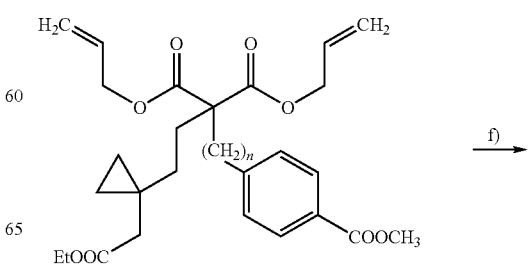

-continued

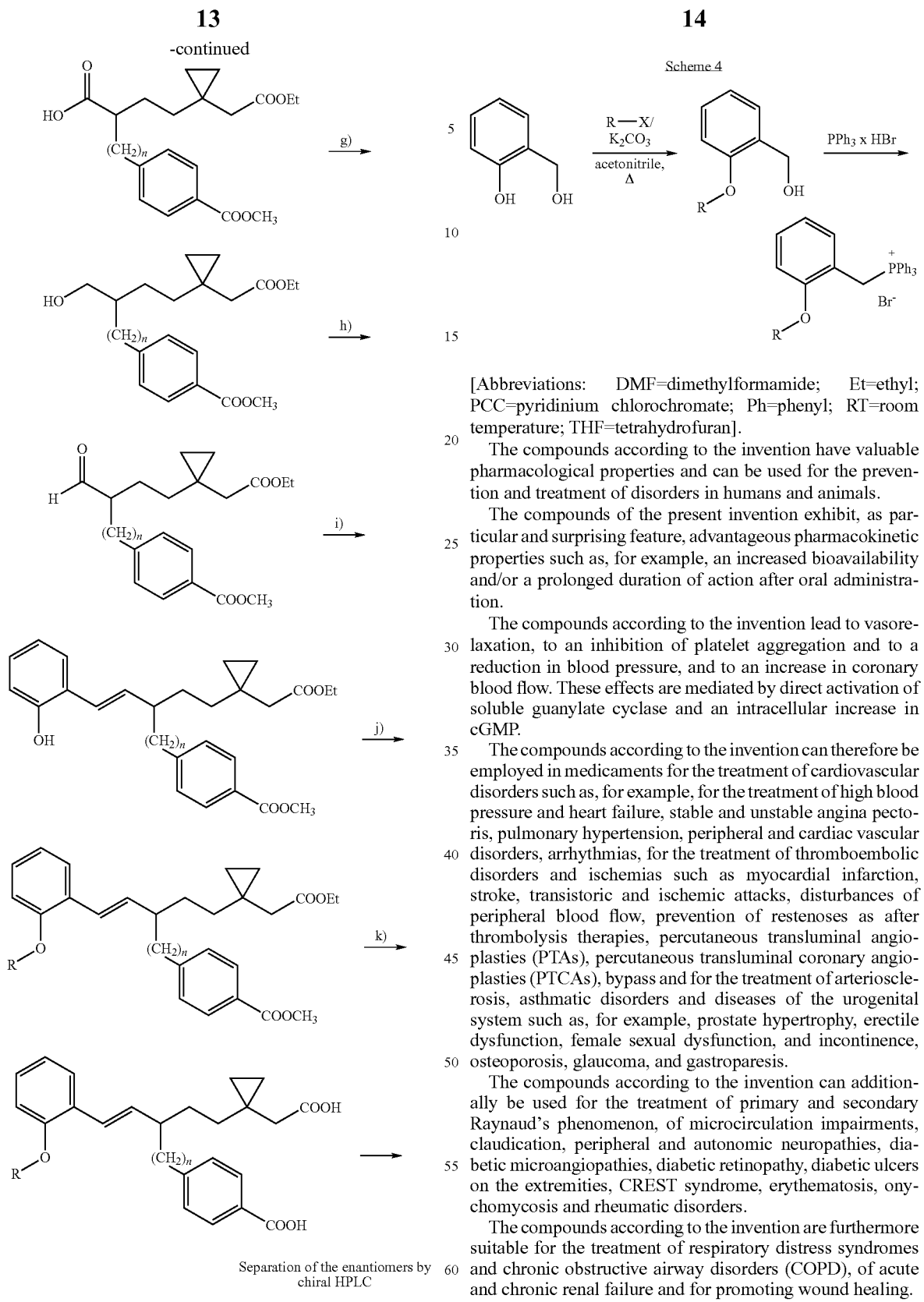

Separation of the enantiomers by chiral HPLC

[f) Palladium acetate, triphenylphosphine, triethylamine, formic acid, dioxane, 100° C., 2-12 h; g) borane-THF complex, THF, -10° C. → 0° C., 2 h; h) PCC, dichloromethane, RT, 12 h; i) (2-hydroxybenzyl)triphenylphosphonium bromide, n-butyllithium, THF/hexane, 0° C., 2 h; j) R—X (X = Cl, Br or I), potassium carbonate, acetonitrile, 80° C., 12 h; k) lithium hydroxide or sodium hydroxide, water, THF or dioxane, 50° C., 12 h].

[Abbreviations: DMF=dimethylformamide; Et=ethyl; PCC=pyridinium chlorochromate; Ph=phenyl; RT=room temperature; THF=tetrahydrofuran].

The compounds according to the invention have valuable pharmacological properties and can be used for the prevention and treatment of disorders in humans and animals.

The compounds of the present invention exhibit, as particular and surprising feature, advantageous pharmacokinetic properties such as, for example, an increased bioavailability and/or a prolonged duration of action after oral administration.

The compounds according to the invention lead to vasorelaxation, to an inhibition of platelet aggregation and to a reduction in blood pressure, and to an increase in coronary blood flow. These effects are mediated by direct activation of soluble guanylate cyclase and an intracellular increase in cGMP.

The compounds according to the invention can therefore be employed in medicaments for the treatment of cardiovascular disorders such as, for example, for the treatment of high blood pressure and heart failure, stable and unstable angina pectoris, pulmonary hypertension, peripheral and cardiac vascular disorders, arrhythmias, for the treatment of thromboembolic disorders and ischemias such as myocardial infarction, stroke, transistoric and ischemic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, CREST syndrome, erythematosis, onychomycosis and rheumatic disorders.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions (Apoplexia cerebri) such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:

organic nitrates and NO donors such as, for example, sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;

NO-independent but heme-dependent stimulators of guanylate cyclase, such as, in particular, the compounds described in WO 00/06568, WO 00/06569, WO 02/42301 and WO 03/095451;

agents having antithrombotic activity, for example and preferably from the group of platelet aggregation inhibitors, of anticoagulants or of profibrinolytic substances;

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, BAY 59-7939, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein(a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays;

tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations abs. Absolute
aq. Aqueous
CI Chemical ionization (in MS)
DCI Direct chemical ionization (in MS)
DMF Dimethylformamide
DMSO Dimethyl sulfoxide
ee Enantiomeric excess
EI Electron impact ionization (in MS)
eq. Equivalent(s)
ESI Electrospray ionization (in MS)
Ex. Example
GC Gas chromatography
h Hour(s)
HPLC High pressure, high performance liquid chromatography
LC-MS Coupled liquid chromatography-mass spectroscopy
min Minute(s)
MS Mass spectroscopy
NMR Nuclear magnetic resonance spectroscopy
$R_f$ Retention index (in TLC)
RT Room temperature
$R_t$ Retention time (in HPLC)
THF Tetrahydrofuran
TLC Thin-layer chromatography
UV Ultraviolet spectroscopy
v/v Volume to volume ratio (of a solution)

LC/MS Methods:
Method 1 (LC-MS)

MS instrument type: Micromass ZQ; HPLC instrument type: HP 1100 series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS)

MS instrument type: Micromass ZQ; HPLC instrument type: Waters Alliance 2795; column: Phenomenex Synergi 2µ Hydro-R P Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flowrate: 0.0 min 1 ml/min→2.5 min/3.0 min/4.5 min 2 ml/min; oven: 50° C.; UV detection: 210 nm.

Method 3 (LC-MS)

Instrument: Micromass Platform LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4 (LC-MS)

Instrument: Micromass Quattro LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 5 (LC-MS)

Instrument: Micromass Platform LCZ with HPLC Agilent Series 1100; column: Thermo Hypersil GOLD 3µ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC-MS)

MS instrument type: Micromass ZQ; HPLC instrument type: HP 1100 Series; UV DAD; column: Phenomenex Gemini 3µ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm n.

GC/MS Methods:
Method 1 (GC-MS)

Instrument: Micromass GCT, GC6890; column: Restek RTX-35MS, 30 m×250 µm×0.25 µm; constant helium flow: 0.88 ml/min; oven: 60° C.; inlet: 250° C.; gradient: 60° C.

(hold for 0.30 min), 50° C./min→120° C., 16° C./min→250° C., 30° C./min→300° C. (hold for 1.7 min).

Method 2 (GC-MS)

Instrument: Micromass GCT, GC6890; column: Restek RTX-35MS, 30 m×250 μm×0.25 μm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 8.7 min).

HPLC Methods:

Method 1 (HPLC)

Instrument: HP 1100 with DAD detection; column: Kromasil 100 RP-18, 60 mm×2.1 mm, 3.5 μm; eluent A: 5 ml of HClO$_4$ (70%)/l of water, eluent B: acetonitrile; gradient: 0 min 2% B→0.5 min 2% B→4.5 min 90% B→9 min 90% B→9.2 min 2% B→10 min 2% B; flow rate: 0.75 ml/min; column temperature: 30° C.; UV detection: 210 nm.

Method 2 (HPLC)

Instrument: HP 1100 with DAD detection; column: Kromasil 100 RP-18, 60 mm×2.1 mm, 3.5 μm; eluent A: 5 ml of HClO$_4$ (70%)/l of water, eluent B: acetonitrile; gradient: 0 min 2% B→0.5 min 2% B→4.5 min 90% B→15 min 90% B→15.2 min 2% B→16 min 2% B; flow rate: 0.75 ml/min; column temperature: 30° C.; UV detection: 210 nm.

Starting Materials and Intermediates

Example 1A

Ethyl cyclopropylideneacetate

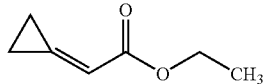

A suspension of 38.49 g (220.80 mmol) of [(1-ethoxycyclopropyl)oxy](trimethyl)silane, 100.0 g (287.04 mmol) of ethyl (triphenylphosphoranylidene)acetate and 3.51 g (28.70 mmol) of benzoic acid in 600 ml of toluene is stirred at a bath temperature of 90° C. for 18 hours. After cooling, the mixture is poured onto 800 g of silica gel 60 and eluted successively with in each case 3 liters of petroleum ether 40-60 and dichloromethane. The dichloromethane eluate is, after removal of the solvent, distilled at 160° C. and 14 mbar in a kugelrohr. This gives 17.95 g (64% of theory) of the title compound as a colorless liquid.

GC-MS (method 1): R$_t$=3.38 min; MS: m/z=98 [M-28]$^+$.

$^1$H-NMR (400 MHz, CDCl$_3$): δ=1.23 (m, 2H), 1.31 (t, 3H), 1.45 (m, 2H), 4.21 (q, 2H), 6.23 (m, 1H).

Example 2A

Ethyl (1-vinylcyclopropyl)acetate

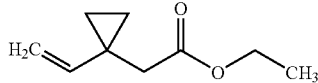

Under argon, 0.55 g (5.53 mmol) of copper(I) chloride and 0.59 g (13.82 mmol) of lithium chloride are suspended in 150 ml of anhydrous THF. The reaction mixture is cooled to −78° C., 48.8 ml (82.95 mmol) of vinylmagnesium chloride solution (1.7 M in THF) are added and the mixture is stirred for 10 minutes. Over a period of 30 min, a solution of 8.72 g (69.12 mmol) of ethyl cyclopropylideneacetate (Example 1A) in 50 ml of anhydrous THF is then added dropwise. After the addition is ended, the cooling bath is replaced by an ice/acetone bath. After a further 15 min, the reaction is terminated by dropwise addition of 100 ml of 1 N hydrochloric acid. The reaction mixture is saturated with sodium chloride, and 100 ml of a saturated sodium chloride solution which contains 5 ml of a 25% strength aqueous ammonia solution are then added. The mixture is filtered through Celite. The filtrate is washed with ammoniacal sodium chloride solution until the aqueous phase remains colorless. The organic phase is washed with saturated sodium chloride solution and dried over anhydrous magnesium sulfate. Removal of the solvent and kugelrohr distillation of the residue at 150° C. and 15 mbar gives 7.10 g (67% of theory) of the title compound as a colorless liquid.

GC-MS (method 1): R$_t$=3.60 min; MS: m/z=154 [M]$^+$.

$^1$H-NMR (400 MHz, CDCl$_3$): δ=0.73 (m, 2H), 0.77 (m, 2H), 1.25 (t, 3H), 2.42 (s, 2H), 4.14 (q, 2H), 4.92 (d, 1H), 4.95 (d, 1H), 5.55 (dd, 1H).

Example 3A

Ethyl [1-(2-bromoethyl)cyclopropyl]acetate

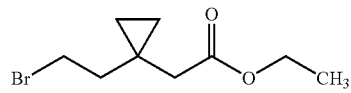

Under argon, 30.86 ml (30.86 mmol) of borane/THF complex solution (1 M in THF) are added dropwise at 0° C. to a solution of 14.00 g (90.79 mmol) of ethyl (1-vinylcyclopropyl)acetate (Example 2A) in 80 ml of anhydrous THF. After 30 min at 0° C., the mixture is stirred at room temperature for a further 30 min, and 0.20 ml (5.00 mmol) of methanol is then added. At −5° C., 5.61 ml (108.94 mmol) of bromine and 26.98 g (150.0 mmol) of sodium methoxide solution (30% strength in methanol) are then successively added dropwise to the reaction mixture. After the mixture has reached room temperature, 30 ml of saturated sodium bicarbonate solution are added. The reaction mixture is extracted three times with tert-butyl methyl ether. The combined organic phases are washed with saturated sodium chloride solution and dried over anhydrous magnesium sulfate. Removal of the solvent and kugelrohr distillation of the residue at 180° C. and 0.04 mbar gives 12.90 g (60% of theory) of the title compound as a yellow oil which, on storage in a fridge, turns very dark over a period of a few hours.

GC-MS (method 1): R$_t$=5.94 min; MS: m/z=189 [M-45]$^+$.

$^1$H-NMR (400 MHz, CDCl$_3$): δ=0.49 (m, 2H), 0.51 (m, 2H), 1.27 (t, 3H), 1.93 (t, 2H), 2.25 (s, 2H), 3.48 (t, 2H), 4.14 (q, 2H).

Example 4A

Diallyl 2-[4-(methoxycarbonyl)phenyl]ethylmalonate

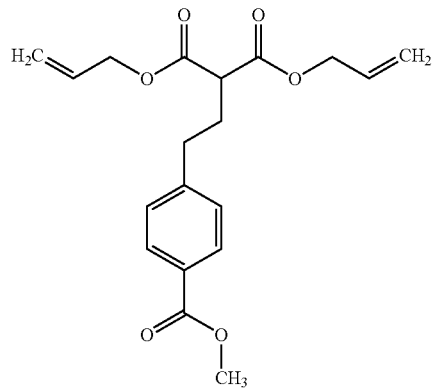

Under argon and at 0° C., 4.44 g (111.0 mmol) of sodium hydride (60% strength dispersion in mineral oil) are added a little at a time to a solution of 27.28 g (148.09 mmol) of diallyl malonate in 220 ml of anhydrous dioxane. The mixture is stirred at 40° C. for 30 min, and a solution of 18.00 g (74.04 mmol) of methyl 4-(2-bromoethyl)benzoate is then added at room temperature. The reaction mixture is then heated at 110° C. for 16 hours. After addition of 25 ml of saturated ammonium chloride solution, most of the dioxane is removed on a rotary evaporator. The residue is taken up in 200 ml of ethyl acetate and 100 ml of water. The aqueous phase is extracted with ethyl acetate. The combined organic phases are washed with saturated sodium chloride solution and dried over anhydrous magnesium sulfate. After distillative removal of a large proportion of the excess diallyl malonate, the crude product is pre-purified on 100 g of silica gel 60 (mobile phase: cyclohexane/dichloromethane 2:1, then cyclohexane/ethyl acetate 4:1). The desired product is then isolated by preparative HPLC. This gives 11.60 g (22% of theory) of a colorless oil.

LC-MS (method 2): $R_t$=2.53 min; MS (ESIpos): m/z=347 [M+H]$^+$.

$^1$H-NMR (400 MHz, CDCl$_3$): δ=2.26 (m, 2H), 2.73 (t, 2H), 3.40 (t, 1H), 3.91 (s, 3H), 4.63 (d, 4H), 5.25 (d, 2H), 5.33 (d, 2H), 5.90 (m, 2H), 7.25 (d, 2H), 7.96 (d, 2H).

Example 5A

Diallyl {2-[1-(2-ethoxy-2-oxoethyl)cyclopropyl]ethyl}{2-[4-(methoxycarbonyl)phenyl]ethyl}-malonate

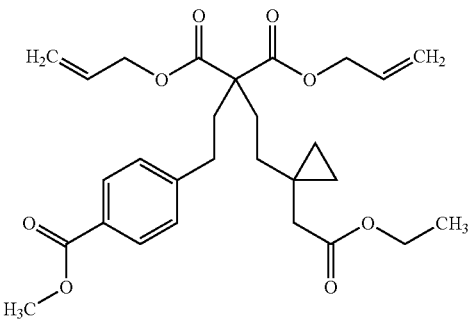

Under argon and at 0° C., 0.22 g (5.41 mmol) of sodium hydride (60% strength dispersion in mineral oil) is added a little at a time to a solution of 1.34 g (3.87 mmol) of diallyl 2-[4-(methoxy-carbonyl)phenyl]ethylmalonate in 10 ml of anhydrous DMF. The mixture is stirred at 40° C. for 30 min, and a solution of 1.00 g (4.25 mmol) of ethyl [1-(2-bromoethyl)cyclopropyl]acetate in 5 ml of anhydrous DMF is then added dropwise at this temperature. The reaction mixture is then heated at 110° C. for 12 hours. After addition of 100 ml of water and 100 ml of ethyl acetate and phase separation, the aqueous phase is extracted with ethyl acetate. The organic phase is then washed five times with water and once with saturated sodium chloride solution and dried over anhydrous magnesium sulfate. The crude product is purified by preparative HPLC. This gives 0.33 g (17% of theory) of the title compound as a colorless oil.

LC-MS (method 2): $R_t$=3.02 min; MS (ESIpos): m/z=501 [M+H]$^+$.

$^1$H-NMR (400 MHz, CDCl$_3$): δ=0.35 (m, 2H), 0.47 (m, 2H), 1.23 (t, 3H), 1.26 (m, 2H), 2.10 (m, 2H), 2.16 (m, 2H), 2.25 (s, 2H), 2.58 (m, 2H), 3.90 (s, 3H), 4.11 (q, 2H), 4.61 (d, 4H), 5.24 (m, 2H), 5.32 (m, 2H), 5.88 (m, 2H), 7.24 (d, 2H), 7.94 (d, 2H).

Example 6A

4-[1-(2-Ethoxy-2-oxoethyl)cyclopropyl]-2-{2-[4-(methoxycarbonyl)phenyl]ethyl}butanoic acid

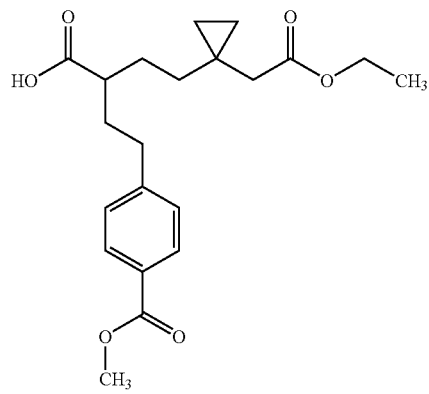

At room temperature a solution of 0.6 ml (4.3 mmol) of triethylamine and 0.12 ml (3.25 mmol) of formic acid in 15 ml of dioxane is added to a solution of 650 mg (1.3 mmol) of diallyl {2-[1-(2-ethoxy-2-oxoethyl)cyclopropyl]ethyl}{2-[4-(methoxycarbonyl)phenyl]ethyl}malonate, 24 mg (0.09 mmol) of triphenylphosphine and 6 mg (0.026 mmol) of palladium acetate in 15 ml of dioxane. The reaction mixture is then stirred at 100° C. for 12 hours. After complete conversion, the reaction solution is cooled and the solvent is removed under reduced pressure. The residue is then taken up in ethyl acetate and water and acidified with 1 N hydrochloric acid, and the organic phase is removed. The aqueous phase is extracted three more times with ethyl acetate, and the organic phases are then combined, washed with saturated sodium chloride solution and dried over sodium sulfate. After filtration, the solution is concentrated under reduced pressure and the residue is purified by flash chromatography on silica gel (mobile phase: cyclohexane/ethyl acetate 4:1). This gives 406 mg (83% of theory) of a yellow oil.

LC-MS (method 4): $R_t$=2.55 min; m/z=377 [M+H]$^+$.

Example 7A

Methyl 4-[5-[1-(2-ethoxy-2-oxoethyl)cyclopropyl]-3-(hydroxymethyl)pentyl]benzoate

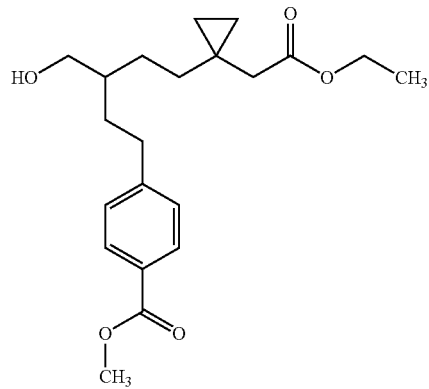

At −10° C., 2.13 ml of a 1 M borane/THF complex solution (2.13 mmol) are added dropwise to a solution of 400 mg (1.06 mmol) of 4-[1-(2-ethoxy-2-oxoethyl)cyclopropyl]-2-{2-[4-(methoxy-carbonyl)phenyl]ethyl}butanoic acid in 10 ml of THF. After warming to 0° C., the mixture is stirred at this temperature for another 2 hours. After complete conversion, saturated ammonium chloride solution is added, and the reaction mixture is extracted three times with 20 ml of ethyl acetate. The combined organic phases are then dried over sodium sulfate, and the solvent is evaporated to dryness. This gives 330 mg (85% of theory) of a colorless oil.

LC-MS (method 2): $R_t$, =2.42 min; m/z=363 [M+H$^+$].

Example 8A

Methyl 4-{5-[1-(2-ethoxy-2-oxoethyl)cyclopropyl]-3-formylpentyl}benzoate

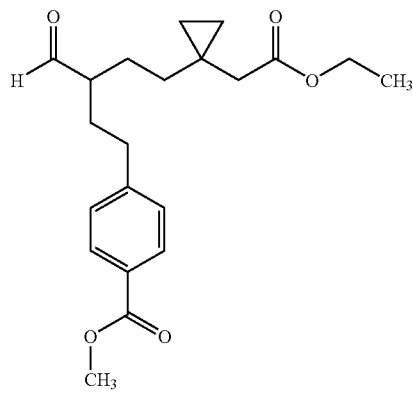

235.5 mg (1.09 mmol) of pyridinium chlorochromate (PCC) are added to a solution of 330 mg (0.91 mmol) of methyl 4-[5-[1-(2-ethoxy-2-oxoethyl)cyclopropyl]-3-(hydroxymethyl)pentyl]-benzoate in 30 ml of dichloromethane, and the mixture is stirred at room temperature for 12 hours.

After complete conversion, 10 g of silica gel are added and the solvent is carefully removed to dryness under reduced pressure. The residue is purified by flash chromatography on silica gel (mobile phase: cyclohexane/ethyl acetate 4:1). This gives 192 mg (58% of theory) of a colorless oil.

LC-MS (method 2): $R_t$=2.56 min; m/z=361 [M+H$^+$].

Example 9A

Methyl 4-[(4E)-3-{2-[1-(2-ethoxy-2-oxoethyl)cyclopropyl]ethyl}-5-(2-hydroxyphenyl)pent-4-en-1-yl]benzoate

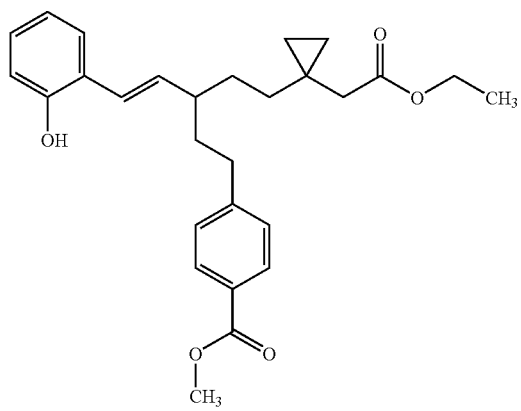

At 0° C., 0.6 ml (1.5 mmol) of a 2.5 M solution of n-butyllithium in hexane is slowly added to a solution of 359 mg (0.799 mmol) of (2-hydroxybenzyl)triphenylphosphonium bromide in 5 ml of anhydrous THF, and the mixture is stirred for 45 min. At this temperature, 192 mg (0.53 mmol) of methyl 4-{5-[1-(2-ethoxy-2-oxoethyl)cyclopropyl]-3-formylpentyl}benzoate are then added slowly, and the mixture is stirred at 0° C. for 2 hours. After complete conversion, saturated ammonium chloride solution is added to the reaction solution, which is then concentrated to dryness. The residue is taken up in ethyl acetate, washed with water and saturated sodium chloride solution and dried over sodium sulfate. After filtration, the solvent is evaporated to dryness. The crude product obtained is purified by flash chromatography on silica gel (mobile phase: cyclohexane/ethyl acetate 4:1). This gives 178.5 mg (74% of theory) of a colorless oil.

LC-MS (method 1): R=3.25 min; m/z=451[M+H$^+$].

Example 10A

Methyl 4-((4E)-5-{2-[(4-tert-butylbenzyl)oxy]phenyl}-3-{2-[1-(2-ethoxy-2-oxoethyl)cyclopropyl]-ethyl}pent-4-en-1-yl)benzoate

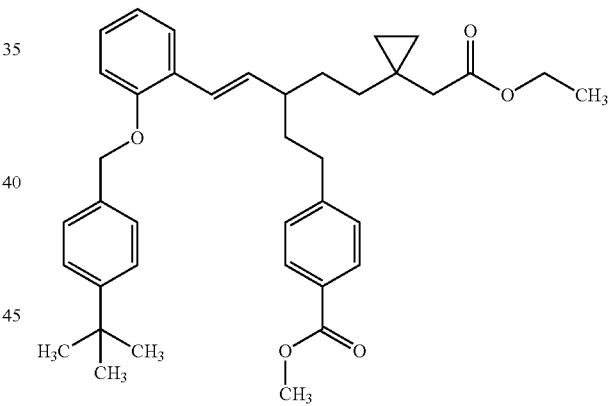

134.6 mg (0.59 mmol) of 4-(tert-butyl)benzyl bromide and 163.8 mg (1.18 mmol) of anhydrous potassium carbonate are added to a solution of 178 mg (0.395 mmol) of methyl 4-[(4E)-3-{2-[1-(2-ethoxy-2-oxoethyl)cyclopropyl]ethyl}-5-(2-hydroxyphenyl)pent-4-en-1-yl]benzoate in 5 ml of dry acetonitrile, and the mixture is heated under reflux for 12 hours. The mixture is then concentrated to dryness. The residue is taken up in ethyl acetate, washed with water and saturated sodium chloride solution and dried over sodium sulfate. The organic phase is concentrated. The crude product obtained is purified by flash chromatography on silica gel (mobile phase: cyclohexane/ethyl acetate 10:1). This gives 130.6 mg (55% of theory) of a solid.

LC-MS (method 1): $R_t$=3.74 min; m/z=597[M+H$^+$].

Example 11A

Diallyl 2-(4-methoxycarbonylbenzyl)malonate

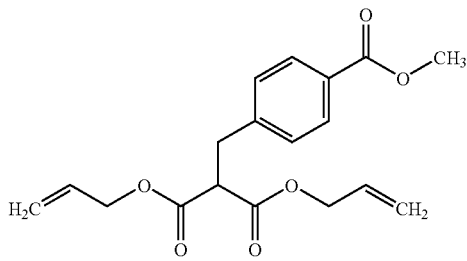

At 0° C., 14.42 g (0.36 mol) of sodium hydride are added a little at a time (careful: evolution of hydrogen) to a solution of 56.7 g (0.3 mol) of diallyl malonate in 375 ml of dioxane and 75 ml of THF. After warming to room temperature, the mixture is stirred at 40° C. for 1 hour. At 40° C., 111.88 g (0.6 mol) of methyl 4-chloromethylbenzoate, dissolved in 375 ml of dioxane, are then slowly added dropwise, and the reaction solution is subsequently stirred at 110° C. (bath temperature) overnight. After cooling to room temperature, the reaction mixture is added to 1200 ml of water. Here, it has to be made sure that the pH is <7 (if appropriate, a few ml of 1 M hydrochloric acid are metered in until the pH is about 2). The mixture is then extracted three times with ethyl acetate, and the combined organic phases are washed with saturated sodium chloride solution and dried over sodium sulfate. After filtration, the solvent is evaporated to dryness under reduced pressure. The crude product obtained is purified by flash chromatography on 3 kg of silica gel (mobile phase: petroleum ether/ethyl acetate 10:1). This gives 85.4 g (0.26 mol, 85% of theory) of a colorless solid.

$^1$H-NMR (300 MHz, CDCl$_3$, δ/ppm): 7.96 (2H, d), 7.29 (2H, d), 5.91-5.74 (2H, m), 5.32-5.17 (4H, m), 4.59 (4H, d), 3.93 (3H, s), 3.74 (1H, t), 3.31 (2H, d).

MS (DCI, NH$_3$): 349 (M+NH$_4^+$).

Example 12A

Diallyl {2-[1-(2-ethoxy-2-oxoethyl)cyclopropyl]ethyl}[4-(methoxycarbonyl)benzyl]malonate

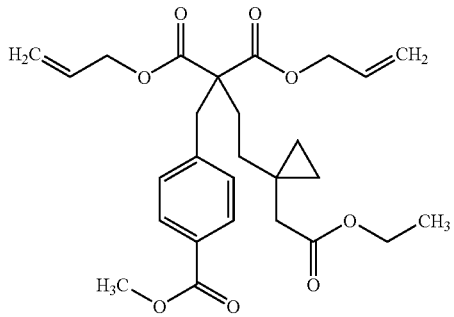

Under argon and at 0° C., 1.67 g (41.62 mmol) of sodium hydride (60% strength dispersion in mineral oil) are added a little at a time to a solution of 10.87 g (32.70 mmol) of diallyl [4-(methoxycarbonyl)benzyl]malonate in 60 ml of anhhdrous DMF. The mixture is stirred at 40° C. for 30 min, and a solution of 6.99 g (29.73 mmol) of ethyl [1-(2-bromoethyl)cyclopropyl]acetate in 60 ml of anhydrous DMF is then added dropwise at this temperature. The reaction mixture is subsequently heated at 100° C. for 8 hours. After addition of 600 ml of water and 200 ml of ethyl acetate and phase separation, the aqueous phase is extracted twice with ethyl acetate. The organic phase is then washed five times with water and once with saturated sodium chloride solution and dried over anhydrous magnesium sulfate. The crude product is initially purified by flash chromatography (400 g of silica gel 60, mobile phase: cyclohexane/ethyl acetate 4:1), and then by preparative HPLC. This gives 4.87 g (28% of theory) of the title compound in the form of a colorless oil.

LC-MS (method 2): R$_t$=2.92 min; MS (ESIpos): m/z=487 [M+H]$^+$.

$^1$H-NMR (400 MHz, CDCl$_3$): δ=0.34 (m, 2H), 0.44 (m, 2H), 1.26 (t, 3H), 1.36 (m, 2H), 1.90 (m, 2H), 2.19 (s, 2H), 3.27 (s, 2H), 3.90 (s, 3H), 4.13 (q, 2H), 4.59 (m, 4H), 5.23 (m, 2H), 5.30 (m, 2H), 5.85 (m, 2H), 7.19 (d, 2H), 7.92 (d, 2H).

Example 13A

4-[1-(2-Ethoxy-2-oxoethyl)cyclopropyl]-2-[4-(methoxycarbonyl)benzyl]butanoic acid

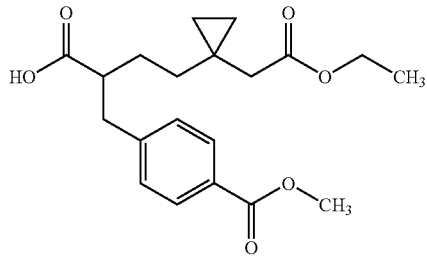

At room temperature, a solution of 4.33 ml (31.06 mmol) of triethylamine and 0.89 ml (23.53 mmol) of formic acid in 20 ml of dioxane is added to a solution of 4.58 g (9.41 mmol) of diallyl {2-[1-(2-ethoxy-2-oxoethyl)cyclopropyl]ethyl}[4-(methoxycarbonyl)benzyl]malonate, 173 mg (0.66 mmol) of triphenylphosphine and 42 mg (0.19 mmol) of palladium acetate in 60 ml dioxane. The reaction mixture is then stirred at 100° C. for 2 hours. After complete conversion, the reaction solution is cooled and the solvent is removed under reduced pressure. The residue is then taken up in ethyl acetate and water and acidified with 1 N hydrochloric acid, and the organic phase is separated off. The aqueous phase is extracted three more times with ethyl acetate, and the organic phases are then combined, washed with saturated sodium chloride solution and dried over sodium sulfate. After filtration, the solution is concentrated under reduced pressure. The crude product obtained is purified by flash chromatography on silica gel (mobile phase: petroleum ether/ethyl acetate 4:1). This gives 2.68 g (73% of theory, 95% purity) of a colorless solid.

$^1$H-NMR (400 MHz, DMSO-d$_6$, δ/ppm): 12.22-12.08 (1H, broad), 7.88 (2H, d), 7.31 (2H, d), 4.02 (2H, q), 3.84 (3H, s), 2.92-2.82 (1H, m), 2.81-2.72 (1H, m), 2.22-2.10 (2H, m), 1.63-1.45 (2H, m), 1.39-1.19 (3H, m), 1.16 (3H, t), 0.41-0.32 (2H, m), 0.31-0.22 (2H, m).

LC-MS (method 1): R$_t$=2.62 min; m/z=363 [M+H]$^+$.

Example 14A

Methyl 4-[4-[1-(2-ethoxy-2-oxoethyl)cyclopropyl]-2-(hydroxymethyl)butyl]benzoate

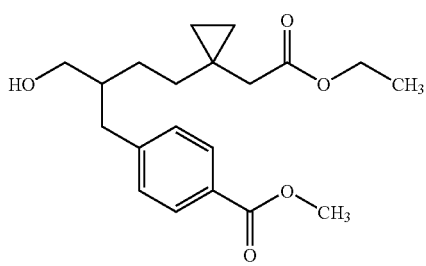

At −10° C., 12.31 ml of a 1 M borane/THF complex solution (12.31 mmol) are added dropwise to a solution of 2.23 g (6.15 mmol) of 4-[1-(2-ethoxy-2-oxoethyl)cyclopropyl]-2-[4-(methoxy-carbonyl)benzyl]butanoic acid in 50 ml of THF. After warming to 0° C., the mixture is stirred at this temperature for another 2 hours and then at room temperature for 1 hour. After complete conversion, saturated ammonium chloride solution is added, and the reaction mixture is extracted three times with in each case 50 ml of ethyl acetate. The combined organic phases are then dried over sodium sulfate, and the solvent is evaporated to dryness. The crude product obtained is purified by flash chromatography on silica gel (mobile phase: cyclohexane/ethyl acetate 2:1). This gives 1680 mg (78% of theory) of a colorless oil.

LC-MS (method 1): $R_t$=2.52 min; m/z=349 [M+H$^+$].

Example 15A

Methyl 4-{4-[1-(2-ethoxy-2-oxoethyl)cyclopropyl]-2-formylbutyl}benzoate

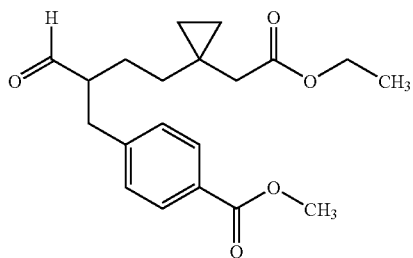

1247 mg (5.79 mmol) of pyridinium chlorochromate (PCC) are added to a solution of 1680 mg (4.82 mmol) of methyl 4-[4-[1-(2-ethoxy-2-oxoethyl)cyclopropyl]-2-(hydroxymethyl)butyl]-benzoate in 100 ml of dichloromethane, and the mixture is stirred at room temperature for 12 hours. After complete conversion, 10 g of silica gel are added and the solvent is carefully removed to dryness under reduced pressure. The residue is purified by flash chromatography on silica gel (mobile phase: cyclohexane/ethyl acetate 4:1). This gives 1270 mg (76% of theory) of a colorless oil.

LC-MS (method 1): $R_t$=2.74 min; m/z=347 [M+H$^+$].

Example 16A

Methyl 4-[(3E)-2-{2-[1-(2-ethoxy-2-oxoethyl)cyclopropyl]ethyl}-4-(2-hydroxyphenyl)but-3-en-1-yl]benzoate

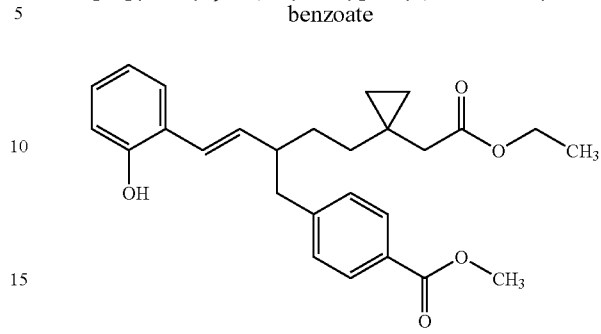

At 0° C., 4.11 ml (10.26 mmol) of a 2.5 M solution of n-butyllithium in hexane are added slowly to a solution of 2.471 g (5.5 mmol) of (2-hydroxybenzyl)triphenylphosphonium bromide in 25 ml of anhydrous THF, and the mixture is stirred for 45 min. At this temperature, 1.27 g (3.67 mmol) of methyl 4-{4-[1-(2-ethoxy-2-oxoethyl)cyclopropyl]-2-formylbutyl}benzoate are then metered in slowly, and the mixture is stirred at 0° C. for two hours. After complete conversion, saturated ammonium chloride solution is added, and the reaction solution is concentrated to dryness. The residue is taken up in ethyl acetate, washed with water and saturated sodium chloride solution and dried over sodium sulfate. After filtration, the solvent is evaporated to dryness. The crude product obtained is purified by flash chromatography on silica gel (mobile phase: cyclohexane/ethyl acetate 4:1). This gives 757 mg (47% of theory) of a yellowish oil.

$^1$H-NMR (400 MHz, DMSO-d$_6$, δ/ppm): 9.41 (1H, s), 7.85 (2H, d), 7.32 (2H, d), 7.28 (1H, d), 6.99 (1H, t), 6.80-6.68 (2H, m), 6.48 (1H, d), 6.04-5.90 (1H, m), 4.00 (2H, q), 3.82 (3H, s), 2.86-2.76 (1H, m), 2.75-2.52 (1H, m), 2.47-2.32 (1H, m), 2.25-2.07 (2H, m), 1.58-1.46 (1H, m), 1.44-1.30 (2H, m), 1.27-1.18 (1H, m), 1.11 (3H, t), 0.41-0.20 (4H, m).

LC-MS (method 4): $R_t$=3.09 min; m/z=437 [M+H$^+$].

Example 17A

Methyl 4-((3E)-4-{2-[(4-tert-butylbenzyl)oxy]phenyl}-2-{2-[1-(2-ethoxy-2-oxoethyl)cyclopropyl]ethyl}but-3-en-1-yl)benzoate

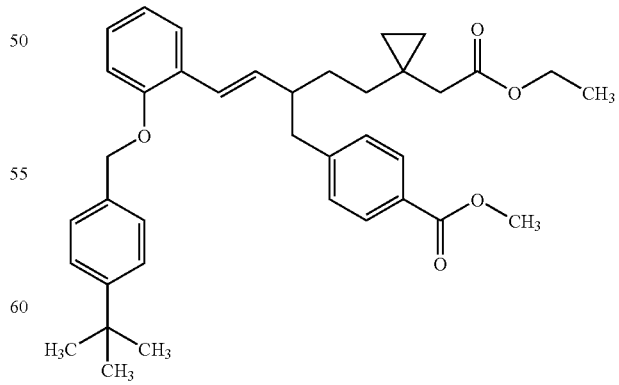

312.2 mg (1.37 mmol) of 4-(tert-butyl)benzyl bromide and 253.3 mg (1.83 mmol) of anhydrous potassium carbonate are added to a solution of 400 mg (0.92 mmol) of methyl 4-[(3E)-

2-{2-[1-(2-ethoxy-2-oxoethyl)cyclopropyl]ethyl})-4-(2-hydroxyphenyl)but-3-en-1-yl]benzoate in 10 ml of dry acetonitrile, and the mixture is heated under reflux for 12 hours. The mixture is then concentrated to dryness. The residue is taken up in ethyl acetate, washed with water and saturated sodium chloride solution and dried over sodium sulfate. The organic phase is concentrated. The crude product obtained is purified by flash chromatography on silica gel (mobile phase: cyclohexane/ethyl acetate 1:1). This gives 289 mg (54% of theory) of a solid.

$^1$H-NMR (400 MHz, DMSO-$d_6$, δ/ppm): 7.84 (2H, d), 7.41-7.34 (3H, m), 7.31 (2H, d), 7.27 (2H, d), 7.15 (1H, t), 7.00 (1H, d), 6.88 (1H, t), 6.42 (1H, d), 6.06-5.96 (1H, m), 5.02 (2H, s), 3.98 (2H, q), 3.81 (3H, s), 2.86-2.78 (1H, m), 2.73-2.62 (1H, m), 2.48-2.38 (1H, m), 2.24-2.10 (2H, m), 1.60-1.49 (1H, m), 1.45-1.33 (2H, m), 1.28 (9H, s), 1.25-1.18 (1H, m), 1.09 (3H, t), 0.40-0.31 (2H, m), 0.30-0.20 (2H, m).

LC-MS (method 1): $R_t$=3.68 min; m/z=600 [M+NH$_4^+$].

Example 18A (5-Bromopentyl)benzene

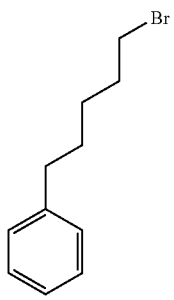

At 0° C., 50 g (0.304 mmol) of 5-phenylpentan-1-ol are added to a solution of 416.7 ml (1.83 mol) of 48% strength hydrobromic acid, and the mixture is stirred at 0° C. for 30 min. The reaction solution is then stirred at 100° C. for 12 hours. After complete conversion, the mixture is cooled to room temperature and 200 ml of ethyl acetate are added. After extraction, the organic phase is separated off, washed with saturated sodium bicarbonate solution and dried over sodium sulfate. After filtration, the filtrate is concentrated to dryness. The crude product obtained is purified by flash chromatography on silica gel (mobile phase: cyclohexane). This gives 59.4 g (0.26 mol, 86% of theory) of a colorless liquid.

$^1$H-NMR (300 MHz, CDCl$_3$, δ/ppm): 7.32-7.22 (2H, m), 7.21-7.11 (3H, m), 3.40 (2H, t), 2.61 (2H, t), 1.97-1.81 (2H, m), 1.72-1.58 (2H, m), 1.56-1.39 (2H, m).

MS (CI): 226 [M+].

Example 19A

Methyl 4-((3E)-2-{2-[1-(2-ethoxy-2-oxoethyl)cyclopropyl]ethyl}-4-{2-[(5-phenylpentyl)oxy]phenyl}but-3-en-1-yl)benzoate

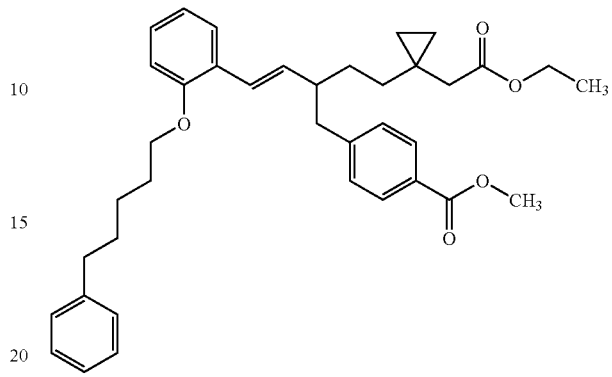

273 mg (1.2 mmol) of (5-bromopentyl)benzene and 222 mg (1.6 mmol) of anhydrous potassium carbonate are added to a solution of 350 mg (0.8 mmol) of methyl 4-[(3E)-2-{2-[1-(2-ethoxy-2-oxoethyl)cyclopropyl]ethyl}-4-(2-hydroxyphenyl)but-3-en-1-yl]benzoate in 10 ml of dry acetonitrile, and the mixture is heated under reflux for 12 hours. The mixture is then concentrated to dryness. The residue is taken up in ethyl acetate, washed with water and saturated sodium chloride solution and dried over sodium sulfate. The organic phase is concentrated. The crude product obtained is purified by flash chromatography on silica gel (mobile phase: cyclohexane/ethyl acetate 9:1). This gives 275 mg (58% of theory) of a solid.

$^1$H-NMR (400 MHz, DMSO-$d_6$, δ/ppm): 7.82 (2H, d), 7.37-7.22 (5H, m), 7.21-7.09 (4H, m), 6.91-6.80 (2H, m), 6.32 (1H, d), 6.04-5.94 (1H, m), 3.99 (2H, q), 3.89 (2H, t), 3.80 (3H, s), 2.85-2.76 (1H, m), 2.73-2.62 (1H, m), 2.59 (2H, t), 2.45-2.32 (1H, m), 2.25-2.19 (2H, m), 1.75-1.49 (5H, m), 1.45-1.32 (4H, m), 1.29-1.15 (1H, m), 1.10 (3H, t), 0.41-0.32 (2H, m), 0.31-0.23 (2H, m).

LC-MS (method 1): $R_t$=3.70 min; m/z=600[M+NH$_4^+$].

Example 20A

Diallyl [4-(tert-butoxycarbonyl)benzyl]malonate

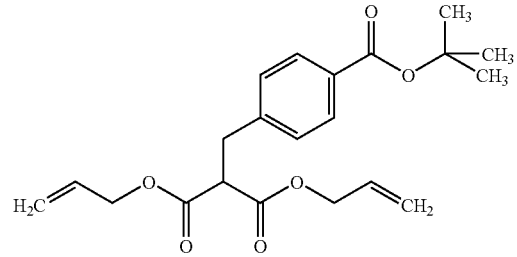

At 0° C., 6.29 g (0.16 mol) of sodium hydride (careful: evolution of hydrogen) are added a little at a time to a solution of 48.24 g (0.26 mol) of diallyl malonate in 100 ml of dioxane and 40 ml of THF. After warming to room temperature, the mixture is stirred at 40° C. for 1 hour. At 40° C., 29.69 g (0.13 mol) of tert-butyl 4-chloromethylbenzoate, dissolved in 100 ml of dioxane and 40 ml of THF, are slowly added dropwise, and the reaction solution is then stirred at a bath temperature of 110° C. overnight. After cooling to room temperature, 40 ml of saturated ammonium chloride solution and 100 ml of water are added carefully to the reaction mixture. The mixture is then extracted three times with ethyl acetate, and the combined organic phases are washed with saturated sodium chloride solution and dried over sodium sulfate. After filtration, the solvent is evaporated to dryness under reduced pressure. The crude product obtained is purified by flash chromatography on 2 kg of silica gel (mobile phase: petroleum ether/ethyl acetate 20:1). This gives 30.4 g (81 mmol, 62% of theory) of a colorless solid.

LC-MS (method 2): $R_t$=2.90 min; MS (ESIpos): m/z=375 [M+H]$^+$.

Example 21A

Diallyl [4-(tert-butoxycarbonyl)benzyl]{2-[1-(2-ethoxy-2-oxoethyl)cyclopropyl]ethyl}malonate

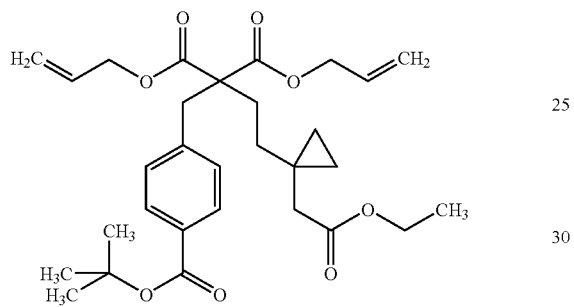

A solution of 19.85 g (43.4 mmol, purity 81.85%) of diallyl [4-(tert-butoxycarbonyl)benzyl]-malonate, 13.94 g (47.7 mmol, purity 80.5%) of ethyl [1-(2-bromoethyl)cyclopropyl] acetate and 28.56 g (87 mmol) of cesium carbonate in 310 ml of acetonitrile is stirred under reflux for 24 hours. The reaction mixture is then filtered, and the filtrate is concentrated to dryness. The crude product is purified by flash chromatography (3000 g of silica gel 60, mobile phase: cyclohexane/ethyl acetate 20:1). This gives 8 g (35% of theory) of the title compound in the form of a colorless oil.

LC-MS (method 4): $R_t$,=3.36 min; MS (ESIpos): m/z=529 [M+H]$^+$.

Example 22A

2-[4-(tert-Butoxycarbonyl)benzyl]-4-[1-(2-ethoxy-2-oxoethyl)cyclopropyl]butanoic acid

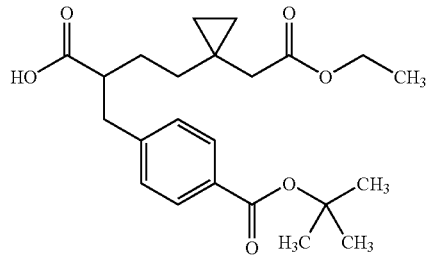

At room temperature, a solution of 7.42 ml (53.56 mmol) of triethylamine and 1.53 ml (40 mmol) of formic acid in 25 ml of dioxane is added to a solution of 8.58 g (16.2 mmol) of diallyl [4-(tert-butoxycarbonyl)benzyl]{2-[1-(2-ethoxy-2-oxoethyl)cyclopropyl]ethyl}malonate, 298 mg (1.14 mmol) of triphenylphosphine and 73 mg (0.33 mmol) of palladium acetate in 75 ml of dioxane. The reaction mixture is then stirred at 100° C. for 2 hours. After complete conversion, the reaction solution is cooled and the solvent is removed under reduced pressure. The residue is then taken up in ethyl acetate and water and acidified with 1 N hydrochloric acid (pH 4-5), and the organic phase is separated off. The aqueous phase is extracted three more times with ethyl acetate, and the organic phases are then combined, washed with saturated sodium chloride solution and dried over sodium sulfate. After filtration, the solution is concentrated under reduced pressure. The crude product obtained is purified by flash chromatography on silica gel (700 g; mobile phase: petroleum ether/ethyl acetate 1:1). This gives 4.9 g (74.6% of theory) of a colorless solid.

$^1$H-NMR (400 MHz, DMSO-d$_6$, δ/ppm): 12.14 (1H, br. s), 7.80 (2H, d), 7.29 (2H, d), 4.02 (2H, q), 2.90-2.69 (2H, m) 2.23-2.10 (2H, m), 1.61-1.43 (3H, m), 1.54 (9H, s), 1.39-1.19 (2H, m), 1.15 (3H, t), 0.42-0.32 (2H, m), 0.32-0.21 (2H, m).

LC-MS (method 6): $R_t$=2.84 min; m/z=405 [M+H$^+$].

Example 23A tert-Butyl 4-{4-[1-(2-ethoxy-2-oxoethyl)cyclopropyl]-2-(hydroxymethyl)butyl}benzoate

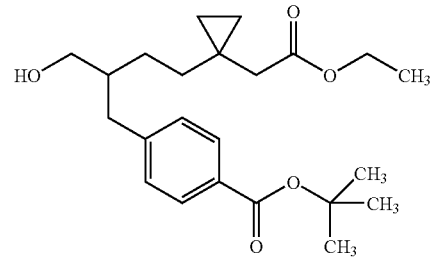

At −10° C., 25.71 ml (25.71 mmol) of a 1 M borane/THF complex solution are added dropwise to a solution of 5199 mg (12.85 mmol) of 2-[4-(tert-butoxycarbonyl)benzyl]-4-[1-(2-ethoxy-2-oxo-ethyl)cyclopropyl]butanoic acid in 100 ml of THF. After warming to 0° C., the mixture is stirred at this temperature for another two hours and then at room temperature for another hour. After complete conversion, saturated ammonium chloride solution is added, and the reaction mixture is extracted three times with in each case 50 ml of ethyl acetate. The combined organic phases are then dried over sodium sulfate, and the solvent is removed to dryness. The crude product obtained is purified by flash chromatography on silica gel (mobile phase: cyclohexane/ethyl acetate 2:1). This gives 3412 mg (68% of theory) of a colorless oil.

LC-MS (method 4): $R_t$=2.52 min; m/z=391 [M+H$^+$].

Example 24A tert-Butyl 4-{4-[1-(2-ethoxy-2-oxoethyl)cyclopropyl]-2-formylbutyl}benzoate

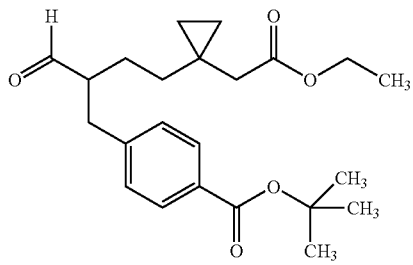

846 mg (3.93 mmol) of pyridinium chlorochromate (PCC) are added to a solution of 1278 mg (3.27 mmol) of tert-butyl 4-{4-[1-(2-ethoxy-2-oxoethyl)cyclopropyl]-2-(hydroxymethyl)-butyl}benzoate in 60 ml of dichloromethane, and the mixture is stirred at room temperature for 12 hours. After complete conversion, 5 g of silica gel are added and the solvent is carefully removed to dryness under reduced pressure. The residue is purified by flash chromatography on silica gel (mobile phase: cyclohexane/ethyl acetate 3:1). This gives 1080 mg (85% of theory) of a colorless oil.

LC-MS (method 6): $R_t$, =3.13 min; m/z=389 [M+H$^+$].

Example 25A tert-Butyl 4-[(3E)-2-{2-[1-(2-ethoxy-2-oxoethyl)cyclopropyl]ethyl}-4-(2-hydroxyphenyl)but-3-en-1-yl]benzoate

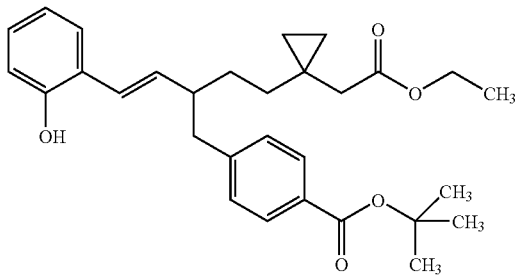

At 0° C., 3.11 ml (7.78 mmol) of a 2.5 M solution of n-butyllithium in hexane are added slowly to a solution of 1.874 g (4.2 mmol) of (2-hydroxybenzyl)triphenylphosphonium bromide in 25 ml of anhydrous THF, and the mixture is stirred for 45 minutes. At this temperature, 1.080 g (2.78 mmol) of tert-butyl 4-{4-[1-(2-ethoxy-2-oxoethyl)cyclopropyl]-2-formylbutyl}benzoate are metered in slowly, and the mixture is stirred at 0° C. for four hours. After complete conversion, saturated ammonium chloride solution is added, and the reaction solution is concentrated to dryness. The residue is taken up in ethyl acetate, washed with water and saturated sodium chloride solution and dried over sodium sulfate. After filtration, the solvent is evaporated to dryness. The crude product obtained is purified by preparative HPLC. This gives 162 mg (8% of theory) of a colorless oil.

LC-MS (method 2): $R_t$=3.19 min; m/z=477 [M−H$^-$].

Example 26A tert-Butyl 4-[(3E)-2-{2-[1-(2-ethoxy-2-oxoethyl)cyclopropyl]ethyl}-4-(2-{[4-(trifluoromethoxy)-benzyl]oxy}phenyl)but-3-en-1-yl]benzoate

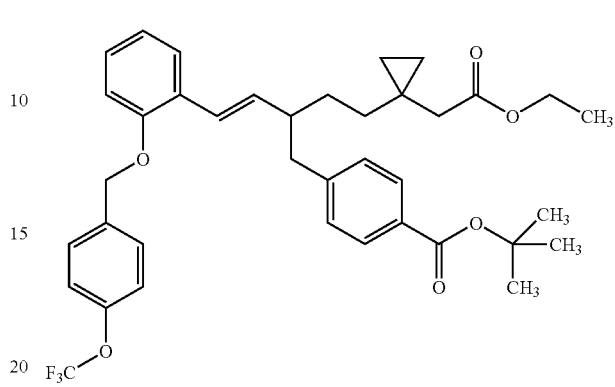

118 mg (0.46 mmol) of 4-trifluoromethoxybenzyl bromide and 98 mg (0.71 mmol) of anhydrous potassium carbonate are added to a solution of 170 mg (0.36 mmol) of tert-butyl 4-[(3E)-2-{2-[1-(2-ethoxy-2-oxoethyl)cyclopropyl]ethyl}-4-(2-hydroxyphenyl)but-3-en-1-yl]benzoate in 3 ml of dry acetonitrile, and the mixture is heated under reflux for 12 hours. The mixture is then concentrated to dryness. The residue is taken up in ethyl acetate, washed with water and saturated sodium chloride solution and dried over sodium sulfate. The organic phase is concentrated. The crude product obtained is purified by flash chromatography on silica gel (mobile phase: cyclohexane/ethyl acetate 5:1). This gives 155 mg (67% of theory) of a colorless oil.

LC-MS (method 6): $R_t$=3.66 min; m/z=670 [M+NH$_4^+$].

Example 27A

4-[(3E)-2-{2-[1-(2-Ethoxy-2-oxoethyl)cyclopropyl]ethyl}-4-(2-{[4-(trifluoromethoxy)benzyl]oxy}-phenyl)but-3-en-1-yl]benzoic acid

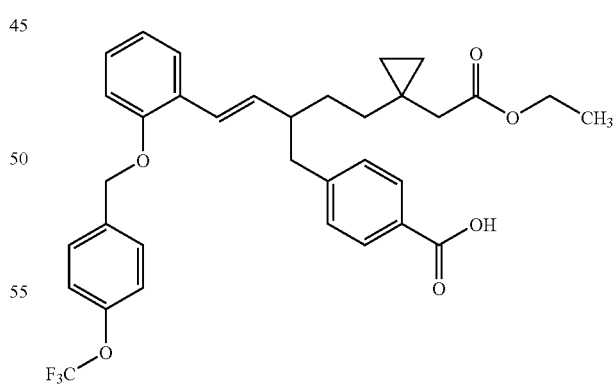

1.5 ml of a 4 N solution of HCl gas in dioxane are added to a solution of 154 mg (0.24 mmol) of tert-butyl 4-[(3E)-2-{2-[1-(2-ethoxy-2-oxoethyl)cyclopropyl]ethyl}-4-(2-{[4-(trifluoromethoxy)-benzyl]oxy}phenyl)but-3-en-1-yl]benzoate, and the mixture is stirred at room temperature for 6 hours. The mixture is concentrated, and the residue is partitioned between water and ethyl acetate. The organic phase is dried over sodium sulfate and concentrated. This gives 140 mg (0.23 mmol, 99% of theory) of the title compound.

LC-MS (method 6): $R_t$=3.34 min; MS (ESIpos): m/z=597 [M+H]$^+$.

140 mg (0.23 mmol) of the racemic 4-[(3E)-2-{2-[1-(2-ethoxy-2-oxoethyl)cyclopropyl]ethyl}-4-(2-{[4-(trifluoromethoxy)benzyl]oxy}phenyl)but-3-en-1-yl]benzoic acid obtained in this manner are separated further by preparative HPLC on a chiral phase. What is obtained are, in each case enantiomerically pure, 51 mg and 71 mg, respectively, of the two E isomers as colorless solids (see Examples 28A and 29A).

Example 28A

4-[(3E)-2-{2-[1-(2-Ethoxy-2-oxoethyl)cyclopropyl]ethyl}-4-(2-{[4-(trifluoromethoxy)benzyl]oxy}-phenyl)but-3-en-1-yl]benzoic acid (enantiomer 1)

Method for the Separation of the Enantiomers:
Column: Daicel Chiralcel OJ-H 250 mm×20 mm, 5 μm; mobile phase: ethanol (with 1% of water and 0.2% of glacial acetic acid)/isohexane 30:70 (v/v); flow rate: 15 ml/min; UV detection: 220 nm; temperature: 40° C.

$R_t$, 8.90 min; purity 97.5%; >99% ee
Yield: 51 mg
LC-MS (method 4): $R_t$=3.32 min; MS (ESIneg): m/z=595 [M−H]$^-$.

Example 29A

4-[(3E)-2-{2-[1-(2-Ethoxy-2-oxoethyl)cyclopropyl]ethyl}-4-(2-{[4-(trifluoromethoxy)benzyl]oxy}-phenyl)but-3-en-1-yl]benzoic acid (enantiomer 2)

Method for the separation of the enantiomers: see Example 28A.
$R_t$ 11.72 min; purity 99%; >96% ee
Yield: 71 mg
LC-MS (method 4): R=3.32 min; MS (ESIneg): m/z=595 [M−H]$^-$.

Exemplary Embodiments

Example 1

4-((4E)-5-{2-[(4-tert-Butylbenzyl)oxy]phenyl}-3-{2-[1-(carboxymethyl)cyclopropyl]ethyl}pent-4-en-1-yl)benzoic acid (racemate)

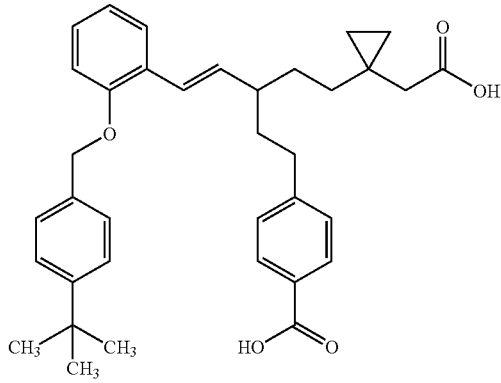

0.69 ml (0.69 mmol) of a 1 M aqueous sodium hydroxide solution is added to a solution of 138 mg (0.23 mmol) of methyl 4-((4E)-5-{2-[(4-tert-butylbenzyl)oxy]phenyl}-3-{2-[1-(2-ethoxy-2-oxoethyl)cyclopropyl]ethyl}pent-4-en-1-yl)benzoate in 3 ml of dioxane, and the mixture is stirred at 50° C. for 12 hours. After cooling, the dioxane is removed under reduced pressure and the aqueous phase is adjusted to pH 4 using 1 M hydrochloric acid. The product precipitates and is filtered off, washed with water and dried. This gives 100.4 mg (78% of theory) of a white solid.

$^1$H-NMR (400 MHz, DMSO d$_6$, δ/ppm): 12.90-11.90 (2H, broad), 7.82 (2H, d), 7.47 (1H, d), 7.39 (4H, s), 7.29 (2H, d), 7.20 (1H, t), 7.08 (1H, d), 6.91 (1H, t), 6.62 (1H, d), 6.09-5.98 (1H, m), 5.11 (2H, s), 2.74-2.63 (1H, m), 2.63-2.51 (1H, m), 2.11-2.00 (1H, m), 1.79-1.68 (1H, m), 1.67-1.47 (2H, m), 1.46-1.13 (5H, m), 1.25 (9H, s), 0.40-0.30 (2H, m), 0.29-0.19 (2H, m).

LC-MS (method 2): $R_t$=3.10 min; nm/z=555 [M+H$^+$].

Using preparative HPLC on a chiral phase, 100 mg (0.18 mmol) of the racemic 4-((4E)-5-{2-[(4-tert-butylbenzyl)oxy]phenyl}-3-{2-[1-(carboxymethyl)cyclopropyl]ethyl}pent-4-en-1-yl)benzoic acid obtained in this manner are separated further. What is obtained are, in each case enantiomerically pure, 6 mg and 20 mg, respectively, of the two E isomers as colorless solids (see Examples 2 and 3).

Example 2

4-((4E)-5-{2-[(4-tert-Butylbenzyl)oxy]phenyl}-3-{2-[1-(carboxymethyl)cyclopropyl]ethyl}pent-4-en-1-yl)benzoic acid (enantiomer 1)

Method for the separation of the enantiomers:
Column: Daicel Chiralpak AD-H 250 mm×20 mm; mobile phase: isohexane (with 1% of water and 0.2% acetic acid)/isopropanol 50:50 (v/v); flow rate: 15 ml/min; UV detection: 220 nm; temperature: 29° C.

$R_t$ 10.05 min; purity>99%; >96% ee
Yield: 6 mg.

Example 3

4-((4E)-5-{2-[(4-tert-Butylbenzyl)oxy]phenyl}-3-{2-[1-(carboxymethyl)cyclopropyl]ethyl}pent-4-en-1-yl)benzoic acid (enantiomer 2)

Method for the separation of the enantiomers: see Example 2.
$R_t$ 13.04 min; purity>99%; >98.5% ee
Yield: 20 mg.

Example 4

4-((3E)-4-{2-[(4-tert-Butylbenzyl)oxy]phenyl}-2-{2-[1-(carboxymethyl)cyclopropyl]ethyl}but-3-en-1-yl)benzoic acid (racemate)

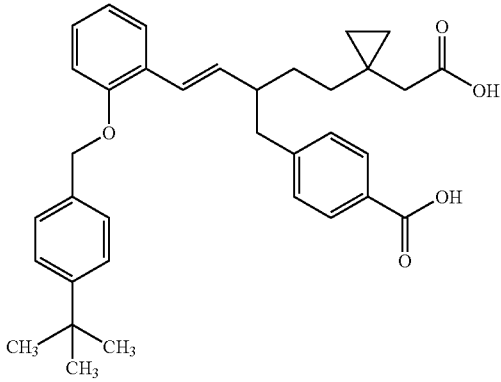

23 mg (0.98 mmol) of lithium hydroxide are added to a solution of 285 mg (0.49 mmol) of methyl 4-((3E)-4-{2-[(4-tert-butylbenzyl)oxy]phenyl}-2-{2-[1-(2-ethoxy-2-oxoethyl)cyclopropyl]ethyl}-but-3-en-1-yl)benzoate in 8 ml of THF and 8 ml of water, and the mixture is stirred at 50° C. for 12 hours. After cooling, the THF is removed under reduced pressure and the aqueous phase is adjusted to pH 4 using 1 M hydrochloric acid. The product precipitates out and is filtered off, washed with water and dried. The crude product obtained in this manner is purified further by flash chromatography on silica gel (mobile phase: dichloromethane/methanol 100:1→50:1→40:1). This gives 179 mg (67% of theory) of a colorless solid.

$^1$H-NMR (400 MHz, DMSO-$d_6$, δ/ppm): 12.80-12.00 (2H, broad), 7.81 (2H, d), 7.42-7.33 (3H, m), 7.31-7.22 (4H, m), 7.14 (1H, t), 7.01 (1H, d), 6.88 (1H, t), 6.42 (1H, d), 6.07-5.97 (1H, m), 5.03 (2H, s), 2.87-2.77 (1H, m), 2.72-2.62 (1H, m), 2.49-2.38 (1H, m), 2.18-2.05 (2H, m), 1.62-1.49 (1H, m), 1.48-1.34 (2H, m), 1.28 (9H, s), 1.25-1.20 (1H, m), 0.39-0.30 (2H, m), 0.29-0.19 (2H, m).

LC-MS (method 1): R=3.16 min; m/z=541 [M+H$^+$].

Using preparative HPLC on a chiral phase, 179 mg (0.33 mmol) of the racemic 4-((3E)-4-{2-[(4-tert-butylbenzyl)oxy]phenyl}-2-{2-[1-(carboxymethyl)cyclopropyl]ethyl}but-3-en-1-yl)benzoic acid obtained in this manner are separated further. What is obtained are, in each case enantiomerically pure, 69 mg and 79 mg, respectively, of the two E isomers as colorless solids (see Examples 5 and 6).

Example 5

4-(3E)-4-{2-[(4-tert-Butylbenzyl)oxy]phenyl}-2-{2-[1-(carboxymethyl)cyclopropyl]ethyl}but-3-en-1-yl)benzoic acid (enantiomer 1)

Method for the separation of the enantiomers:
Column: Daicel Chiralpak AD-H 250 mm×20 mm; mobile phase: isohexane/isopropanol (with 1% of water and 0.2% trifluoroacetic acid) 78:22 (v/v); flow rate: 15 ml/min; UV detection: 220 nm; temperature: 25° C.

R$_t$ 6.97 min; purity>99%; >99.5% ee
Yield: 69 mg
$^1$H-NMR (400 MHz, DMSO-$d_6$, δ/ppm): 12.80-12.00 (2H, broad), 7.81 (2H, d), 7.42-7.33 (3H, m), 7.31-7.22 (4H, m), 7.14 (1H, t), 7.01 (1H, d), 6.88 (1H, t), 6.42 (1H, d), 6.07-5.97 (1H, m), 5.03 (2H, s), 2.87-2.77 (1H, m), 2.72-2.62 (1H, m), 2.49-2.38 (1H, m), 2.18-2.05 (2H, m), 1.62-1.49 (1H, m), 1.48-1.34 (2H, m), 1.28 (9H, s), 1.25-1.20 (1H, m), 0.39-0.30 (2H, m), 0.29-0.19 (2H, m).

Example 6

4-((3E)-4-{2-[(4-tert-Butylbenzyl)oxy]phenyl}-2-{2-[1-(carboxymethyl)cyclopropyl]ethyl}but-3-en-1-yl)benzoic acid (enantiomer 2)

Method for the separation of the enantiomers: see Example 5. R$_t$ 7.61 min; purity>99%; >99.5% ee
Yield: 79 mg
$^1$H-NMR (400 MHz, DMSO-4, δ/ppm): 12.80-12.00 (2H, broad), 7.81 (2H, d), 7.42-7.33 (3H, m), 7.31-7.22 (4H, m), 7.14 (1H, t), 7.01 (1H, d), 6.88 (1H, t), 6.42 (1H, d), 6.07-5.97 (1H, m), 5.03 (2H, s), 2.87-2.77 (1H, m), 2.72-2.62 (1H, m), 2.49-2.38 (1H, m), 2.18-2.05 (2H, m), 1.62-1.49 (1H, m), 1.48-1.34 (2H, m), 1.28 (9H, s), 1.25-1.20 (1H, m), 0.39-0.30 (2H, m), 0.29-0.19 (2H, m).

Example 7

4-((3E)-2-{2-[1-(Carboxymethyl)cyclopropyl]ethyl}-4-{2-[(5-phenylpentyl)oxy]phenyl}but-3-en-1-yl)benzoic acid (racemate)

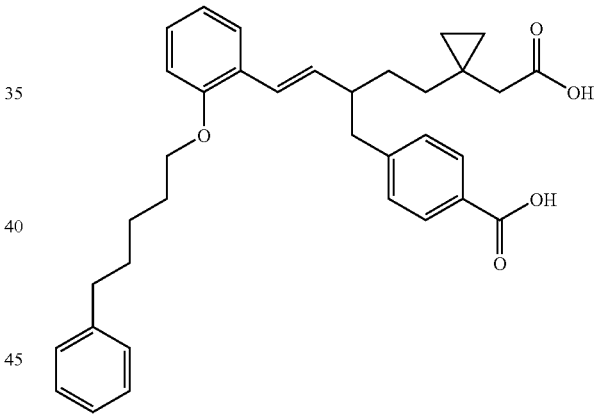

1.39 ml (1.39 mmol) of a 1 M aqueous sodium hydroxide solution are added to a solution of 270 mg (0.46 mmol) of methyl 4-((3E)-2-{2-[1-(2-ethoxy-2-oxoethyl)cyclopropyl]ethyl}-4-{2-[(5-phenylpentyl)oxy]phenyl}but-3-en-1-yl)benzoate in 5 ml of THF, and the mixture is stirred at 50° C. for 12 hours. After cooling, the THF is removed under reduced pressure and the aqueous phase is adjusted to pH 4 using 1 M hydrochloric acid. The product precipitates out and is filtered off, washed with water and dried. This gives 228 mg (91% of theory) of a slightly yellow solid.

LC-MS (method 1): R$_t$=3.18 min; m/z=541 [M+H$^+$].

Using preparative HPLC on a chiral phase, 228 mg (0.42 mmol) of the racemic 4-((3E)-2-{2-[1-(carboxymethyl)cyclopropyl]ethyl}-4-{2-[(5-phenylpentyl)oxy]phenyl}but-3-en-1-yl)benzoic acid obtained in this manner are separated further. What is obtained are, in each case enantiomerically pure, 77 mg and 79 mg, respectively, of the two E isomers as colorless solids (see Examples 8 and 9).

Example 8

4-((3E)-2-{2-[1-(Carboxymethyl)cyclopropyl]ethyl}-4-{2-[(5-phenylpentyl)oxy]phenyl}but-3-en-1-yl)benzoic acid (enantiomer 1)

Method for the separation of the enantiomers:
Column: KBD 6328 [chiral silica gel phase based on the selector poly(N-methacryloyl-L-iso-leucinepentylamide)], 430 mm×40 mm; mobile phase: ethyl acetate; flow rate: 80 ml/min; UV detection: 270 nm; temperature: 24° C.
$R_t$ 6.86 min; purity 99%; >99.5% ee
Yield: 77 mg
$^1$H-NMR (400 MHz, DMSO-$d_6$, δ/ppm): 12.80-11.90 (2H, broad), 7.80 (2H, d), 7.33 (1H, d), 7.30-7.21 (4H, m), 7.20-7.07 (4H, m), 6.93-6.81 (2H, m), 6.34 (1H, d), 6.05-5.94 (1H, m), 3.95-3.78 (2H, m), 2.88-2.74 (1H, m), 2.72-2.61 (1H, m), 2.59 (2H, t), 2.45-2.33 (1H, m), 2.20-2.02 (2H, m), 1.74-1.50 (5H, m), 1.48-1.31 (4H, m), 1.30-1.16 (1H, m), 0.44-0.31 (2H, m), 0.31-0.20 (2H, m).
LC-MS (method 2): $R_t$=2.98 min; MS (ESIneg): m/z=539 [M−H]$^−$.

Example 9

4-((3E)-2-{2-[1-(Carboxymethyl)cyclopropyl]ethyl}-4-{2-[(5-phenylpentyl)oxy]phenyl}but-3-en-1-yl)benzoic acid (enantiomer 2)

Method for the separation of the enantiomers: see Example 8.
$R_t$, 10.04 min; purity 99%; 99.1% ee
Yield: 79 mg
$^1$-NMR (400 MHz, DMSO-$d_6$, δ/ppm): 12.80-11.90 (2H, broad), 7.80 (2H, d), 7.33 (1H, d), 7.30-7.21 (4H, m), 7.20-7.07 (4H, m), 6.93-6.81 (2H, m), 6.34 (1H, d), 6.05-5.94 (1H, m), 3.95-3.78 (2H, m), 2.88-2.74 (1H, m), 2.72-2.61 (1H, m), 2.59 (2H, t), 2.45-2.33 (1H, m), 2.20-2.02 (2H, m), 1.74-1.50 (5H, m), 1.48-1.31 (4H, m), 1.30-1.16 (1H, m), 0.44-0.31 (2H, m), 0.31-0.20 (2H, m).
LC-MS (method 4): $R_t$=3.18 min; MS (ESIneg): m/z=539 [M−H]$^−$.

Example 10

4-[(3E)-2-{2-[1-(Carboxymethyl)cyclopropyl]ethyl}-4-(2-{[4-(trifluoromethoxy)benzyl]oxy}-phenyl)but-3-en-1-yl]benzoic acid (enantiomer 1)

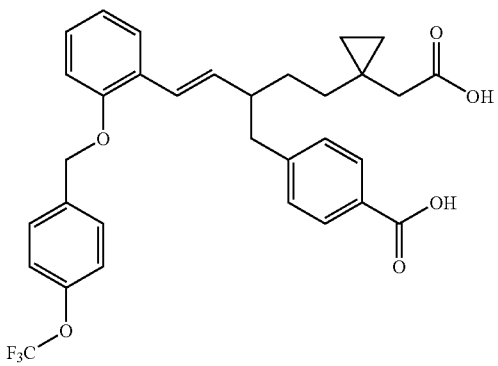

4 mg (0.17 mmol) of lithium hydroxide are added to a solution of 50 mg (0.08 mmol) of 4-[(3E)-2-{2-[1-(2-ethoxy-2-oxoethyl)cyclopropyl]ethyl}-4-(2-{[4-(trifluoromethoxy)benzyl]oxy}phenyl)-but-3-en-1-yl]benzoic acid (enantiomer 1) in 2 ml of THF and 1 ml of water, and the mixture is stirred at 50° C. for 12 hours. After cooling, the THF is removed under reduced pressure, and the aqueous phase is adjusted to pH 4 using 1 M hydrochloric acid. The product precipitates out and is filtered off, washed with water and dried. This gives 38 mg (79% of theory) of a slightly white solid.
$^1$H-NMR (400 MHz, DMSO-$d_6$, δ/ppm): 12.90-11.90 (2H, br. s), 7.81 (2H, d), 7.48 (2H, d), 7.38 (3H, d), 7.28 (2H, d), 7.15 (1H, t), 6.99 (1H, d), 6.90 (1H, t), 6.40 (1H, d), 6.07-5.94 (1H, m), 5.09 (2H, s), 2.89-2.76 (1H, m), 2.73-2.60 (1H, m), 2.47-2.38 (1H, m), 2.19-2.02 (2H, m), 1.63-1.49 (1H, m), 1.48-1.32 (2H, m), 1.31-1.18 (1H, m), 0.40-0.30 (2H, m), 0.29-0.16 (2H, m).
LC-MS (method 2): $R_t$=2.81 min; MS (ESIneg): m/z=567 [M−H]$^−$.

Example 11

4-[(3E)-2-{2-[1-(Carboxymethyl)cyclopropyl]ethyl}-4-(2-{[4-(trifluoromethoxy)benzyl]oxy}-phenyl)but-3-en-1-yl]benzoic acid (enantiomer 2)

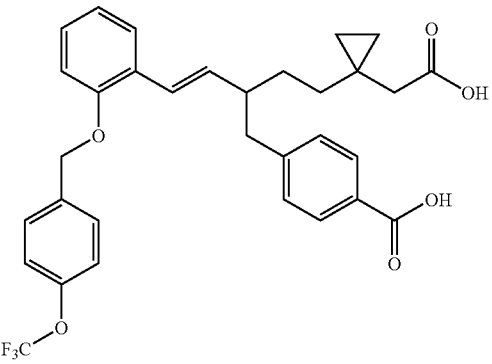

5.6 mg (0.24 mmol) of lithium hydroxide are added to a solution of 70 mg (0.12 mmol) of 4-[(3E)-2-{2-[1-(2-ethoxy-2-oxoethyl)cyclopropyl]ethyl}-4-(2-{[4-(trifluoromethoxy)benzyl]oxy}-phenyl)but-3-en-1-yl]benzoic acid (enantiomer 2) in 1 ml of THF and 0.5 ml of water, and the mixture is stirred at 50° C. for 12 hours. After cooling, the THF is removed under reduced pressure, and the aqueous phase is adjusted to pH 4 using 1 M hydrochloric acid. The product precipitates out and is filtered off, washed with water and dried. This gives 30 mg (45% of theory) of a slightly white solid.
$^1$H-NMR (400 MHz, DMSO-$d_6$, δ/ppm): 12.90-11.90 (2H, br. s), 7.81 (2H, d), 7.48 (2H, d), 7.38 (3H, d), 7.28 (2H, d), 7.15 (1H, t), 6.99 (1H, d), 6.90 (1H, t), 6.40 (1H, d), 6.07-5.94 (1H, m), 5.09 (2H, s), 2.89-2.76 (1H, m), 2.73-2.60 (1H, m), 2.47-2.38 (1H, m), 2.19-2.02 (2H, m), 1.63-1.49 (1H, m), 1.48-1.32 (2H, m), 1.31-1.18 (1H, m), 0.40-0.30 (2H, m), 0.29-0.16 (2H, m).
LC-MS (method 2): $R_t$=2.81 min; MS (ESIneg): m/z=567 [M−H]$^−$.

B. Assessment of the Pharmacological Activity

The pharmacological effect of the compounds according to the invention can be shown in the following assays:

B-1. Vasorelaxant Effect In Vitro:

Rabbits are anesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with carbogen and has the following composition: NaCl 119 mM; KCl 4.8 mM; $CaCl_2 \times 2H_2O$ 1 mM; $MgSO_4 \times 7H_2O$ 1.4 mM; $KH_2PO_4$ 1.2 mM; $NaHCO_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the height of the contraction achieved under the influence of the test substance is compared with the height of the contraction reached in the last preceding run. The concentration necessary to reduce the contraction reached in the preceding control by 50% is calculated from this ($IC_{50}$). The standard application volume is 5 µl. The proportion of DMSO in the bath solution corresponds to 0.1%.

Representative results on the compounds according to the invention are listed in Table 1:

TABLE 1

Vasorelaxant effect in vitro

| Example No. | $IC_{50}$ [nM] |
|---|---|
| 2 | 2.9 |
| 3 | 5.8 |
| 5 | 58 |
| 6 | 33 |
| 8 | 1020 |
| 9 | 406 |

B-2. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the heme-dependent sGC inhibitor 1H-1,2,4-oxadiazole-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The heme-free guanylate cyclase is obtained by adding Tween 20 to the sample buffer (0.5% in the final concentration).

The activation of sGC by a test substance is reported as n-fold stimulation of the basal activity. The result for Example 9 is shown in Table 2:

TABLE 2

Stimulation (n-fold) of recombinant soluble guanylate cyclase (sGC) in vitro by Example 9

| Concentration of Example 9 [µM] | Heme-containing sGC | | | Heme-free sGC Basal |
|---|---|---|---|---|
| | Basal | +0.1 µM DEA/NO | +10 µM ODQ | |
| 0.0 | 1.0 | 101.0 | 3.7 | 1.0 |
| 10 | 8.0 | 109.2 | 41.0 | 21.0 |

[DEA/NO = 2-(N,N-diethylamino)diazenolate 2-oxide; ODQ = 1H-1,2,4-oxadiazole-(4,3a)-quinoxalin-1-one].

It is evident from Table 2 that stimulation both of the heme-containing and of the heme-free enzyme is achieved. Furthermore, combination of Example 9 and 2-(N,N-diethylamino)diazenolate 2-oxide (DEA/NO), an NO donor, shows no synergistic effect, i.e. the effect of DEA/NO is not potentiated as would be expected with an sGC activator acting via a heme-dependent mechanism. In addition, the effect of the sGC activator according to the invention is not blocked by the heme-dependent inhibitor of soluble guanylate cyclase ODQ, but is in fact increased. The results in Table 2 thus confirm the mechanism of action of the compounds according to the invention as activators of soluble guanylate cyclase.

B-3. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitter, (2) receiver which is linked via a multiplexer to a (3) data acquisition computer. The telemetry system makes it possible to record continuously the blood pressure and heart rate on conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 in the morning and at 19.00 in the evening.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area on the side of the abdomen. After the abdominal cavity has been opened along the linea alba, the liquid-filled measuring catheter of the system is inserted into the descending aorta in the cranial direction above the bifurcation and fastened with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of the infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of S ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated from outside by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file bearing the experiment number which is open for this purpose.

In the standard procedure, the following are measured for 10-second periods in each case: (1) systolic blood pressure (SBP), (2) diastolic blood pressure (DBP), (3) mean arterial pressure (MAP) and (4) heart rate (HR).

Measurement acquisition is repeated under computer control at 5-minute intervals. The source data obtained as absolute value are corrected in the diagram with the currently measured barometric pressure and stored in individual data. Further technical details are given in the documentation of the manufacturing company (DSI).

The test substances are administered at 9.00 h on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 h on the day of the experiment to 9.00 h on the following day.

The data are smoothed over a presettable time by determination of the average (15-minute average, 30-minute average) and transferred as text file to a storage medium. The measurements presorted and compressed in this way are transferred into Excel templates and tabulated.

C. Exemplary Embodiments of Pharmaceutical Compositions

The compounds according to the invention can be converted into pharmaceutical preparations in the following ways:

Tablet:
Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.
Production:

A mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.
Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:

500 mg of the compound according to the invention, 2.5 g of polysorbate and 97 g of polyethylene glycol 400.20 g of oral solution correspond to a single dose of 100 mg of the compound according to the invention.
Production:

The compound according to the invention is suspended in the mixture of polyethylene glycol and polysorbate with stirring. The stirring process is continued until the compound according to the invention has completely dissolved.

i.v. Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

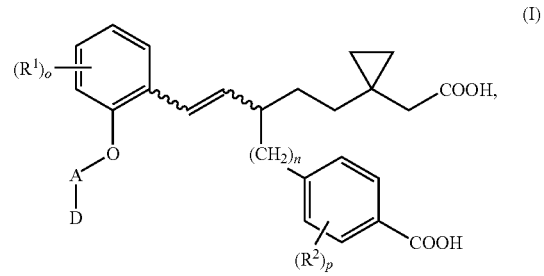

in which

A represents a bond, $(C_1-C_7)$-alkanediyl, $(C_2-C_7)$-alkenediyl or $(C_2-C_7)$-alkynediyl, D represents hydrogen, trifluoromethyl or a group of the formula

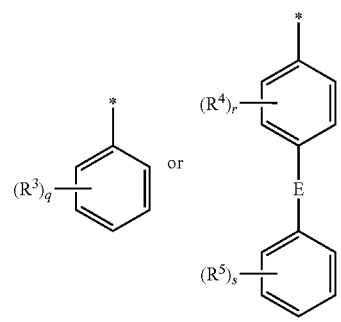

in which * represents the point of attachment to group A and E represents a bond, $CH_2$, —$CH_2$—$CH_2$— or —CH=CH—, n represents the number 1 or 2, $R^1$, $R^2$, $R^3$, $R^4$ and $R^5$ independently of one another represent a substituent selected from the group consisting of halogen, $(C_1-C_6)$-alkyl, trifluoromethyl, $(C_1-C_6)$-alkoxy, trifluoromethoxy, cyano and nitro, and o, p, q, r and s independently of one another each represent the number 0, 1, 2, 3 or 4, where, if $R^1$, $R^2$, $R^3$, $R^4$ or $R^5$ occurs more than once, their meanings may in each case be identical or different, and salts thereof.

2. The compound of the formula (I) as claimed in claim 1, in which
A represents a bond or $(C_1-C_7)$-alkanediyl,
D represents hydrogen, trifluoromethyl or a group of the formula

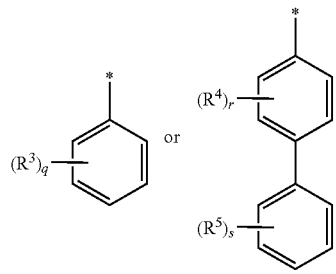

in which * represents the point of attachment to group A,
n represents the number 1 or 2,
$R^1$, $R^3$, $R^4$ and $R^5$ independently of one another represent a substituent selected from the group consisting of fluorine, chlorine, bromine, $(C_1-C_4)$-alkyl, trifluoromethyl, $(C_1-C_4)$-alkoxy and trifluoromethoxy,
o, q, r and s independently of one another each represent the number 0, 1 or 2, where, if $R^1$, $R^3$, $R^4$ or $R^5$ occurs more than once, their meanings may in each case be identical or different,
$R^2$ represents fluorine
and
p represents the number 0 or 1,
and salts thereof.

3. A compound of the formula (I-A)

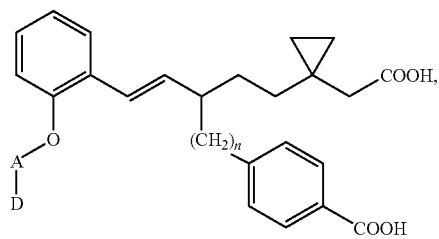
(I-A)

in which
A represents $(C_1-C_7)$-alkanediyl,
D represents hydrogen or a group of the formula

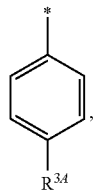

in which * represents the point of attachment to group A
and
$R^{3A}$ represents hydrogen, fluorine, chlorine, methyl, tert-butyl, trifluoromethyl, methoxy or trifluoromethoxy,
and
n represents the number 1 or 2,
and salts thereof.

4. A process for preparing a compound of the formula (I) as defined in claim 1, characterized in that compounds of the formula (II)

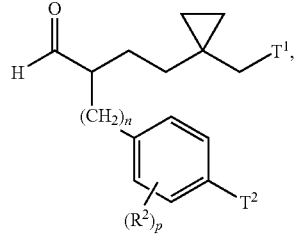
(II)

in which $R^2$, n and p each have the meanings given in claim 1 and $T^1$ and $T^2$ are identical or different and represent cyano or $(C_1-C_4)$-alkoxycarbonyl, are either

[A] reacted in an inert solvent in the presence of a base with a compound of the formula (III-A)

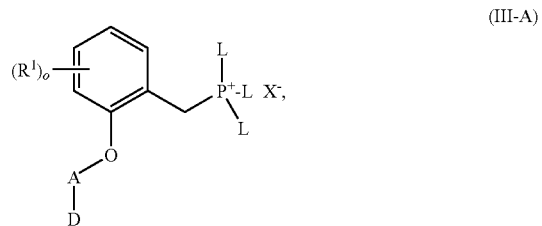
(III-A)

in which A, D, $R^1$ and o each have the meanings given in claim 1 and
L represents phenyl or o-, m- or p-tolyl
and
X represents halide or tosylate,
to give compounds of the formula (IV-A)

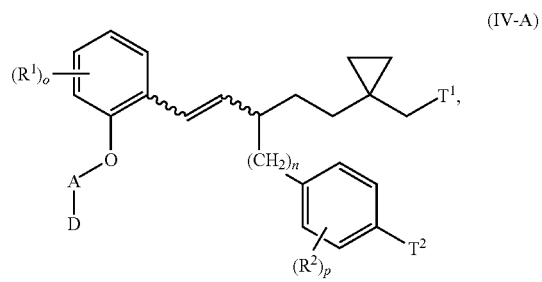
(IV-A)

in which A, D, $R^1$, $R^2$, n, o, p, $T^1$ and $T^2$ each have the meanings given above,
or

[B] reacted in an inert solvent in the presence of a base with a compound of the formula (III-B)

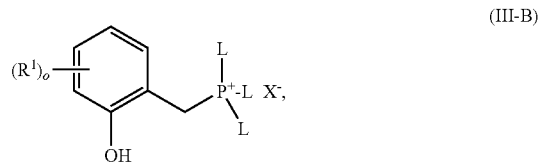
(III-B)

in which $R^1$, o, L and X each have the meanings given above,
initially to give compounds of the formula (IV-B)

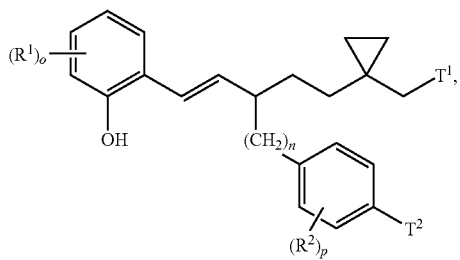

(IV-B)

in which $R^1$, $R^2$, n, o, p, $T^1$ and $T^2$ each have the meanings given above, and these compounds are then alkylated in an inert solvent in the presence of a base with a compound of the formula (V)

D-$A^1$-Q   (V), in which D has the meaning given above, $A^1$ has the meaning of A given in claim 1, but does not represent a bond, and Q represents halogen, tosylate or mesylate, to give compounds of the formula (IV-C)

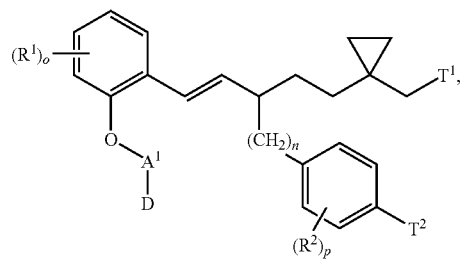

(IV-C)

in which $A^1$, D, $R^1$, $R^2$, n, o, p, $T^1$ and $T^2$ each have the meanings given above, and the resulting compounds of the formula (IV-A) or (IV-C) are then converted by hydrolysis of the ester or nitrile groups $T^1$ and $T^2$ into the dicarboxylic acids of the formula (I)

and the compounds of the formula (I) are, converted with the appropriate (i) solvents and/or (ii) bases or acids into their salts.

5. A pharmaceutical composition comprising a compound of claim 1 in combination with an inert, non-toxic, pharmaceutically suitable excipient.

6. The pharmaceutical composition of claim 5 further comprising an active compound selected from the group consisting of an organic nitrate, an NO donor, an cGMP-PDE inhibitor, a stimulator of guanylate cyclase, an agent having antithrombotic activity, an agent lowering blood pressure, and an agent altering lipid metabolism.

* * * * *